(12) United States Patent
Ito et al.

(10) Patent No.: US 8,710,084 B2
(45) Date of Patent: Apr. 29, 2014

(54) TETRAZOLYL OXIME DERIVATIVE, SALT THEREOF, AND PLANT DISEASE CONTROL AGENT

(75) Inventors: Syuichi Ito, Naka-gun (JP); Kazushige Fujii, Odawara (JP); Hiroyasu Hosokawa, Fujieda (JP); Ichirou Urihara, Tokyo (JP); Atsunori Isshiki, Yokohama (JP)

(73) Assignee: Nippon Soda Co., Ltd., Tokyo (JP)

( * ) Notice: Subject to any disclaimer, the term of this patent is extended or adjusted under 35 U.S.C. 154(b) by 147 days.

(21) Appl. No.: 13/203,911

(22) PCT Filed: Feb. 26, 2010

(86) PCT No.: PCT/JP2010/001345
§ 371 (c)(1),
(2), (4) Date: Aug. 30, 2011

(87) PCT Pub. No.: WO2010/100876
PCT Pub. Date: Sep. 10, 2010

(65) Prior Publication Data
US 2011/0313152 A1   Dec. 22, 2011

(30) Foreign Application Priority Data
Mar. 2, 2009 (JP) .................. 2009-047770

(51) Int. Cl.
*A01N 43/40* (2006.01)
*C07D 401/12* (2006.01)

(52) U.S. Cl.
USPC ........................... 514/340; 546/268.4

(58) Field of Classification Search
USPC ........................... 546/268.4; 514/340
See application file for complete search history.

(56) References Cited

FOREIGN PATENT DOCUMENTS

| | | |
|---|---|---|
| JP | 2003-137875 | 5/2003 |
| JP | 2003-137876 | 5/2003 |
| JP | 2004-131392 | 4/2004 |
| JP | 2004-131416 | 4/2004 |
| WO | 03/016303 | 2/2003 |
| WO | 2008/006873 | 1/2008 |
| WO | 2008/006874 | 1/2008 |
| WO | 2008/006875 | 1/2008 |
| WO | 2008/140099 | 11/2008 |
| WO | 2009/020191 | 2/2009 |
| WO | 2009/130900 | 10/2009 |

OTHER PUBLICATIONS

International Search Report issued for PCT/JP2010/001345, mailed on Mar. 23, 2010, 4 pages.

*Primary Examiner* — Patricia L Morris
(74) *Attorney, Agent, or Firm* — Kenyon & Kenyon, LLP

(57) ABSTRACT

The present invention provide a tetrazolyl oxime derivative represented by formula (1) (in formula (1), X represents a halogen atom or the like, n1 represents an integer of 0 to 5, A represents a tetrazolyl group, Het represents a group represented by formula (4) or the like, in formula (4), R represents a halogen atom or the like, n2 represents an integer of 0 to 3, Z represents a group represented by formula (a), in formula (a), $R^{50}$-$R^{53}$ represents a hydrogen atom or the like, n3 represents an integer of 0 to 2, n4 represents 1 or 2, n5 represents 0 or 1) or salt thereof, and a plant disease control agent containing the same as an active ingredient.

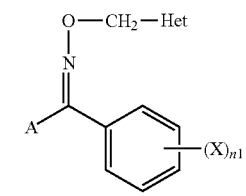

(1)

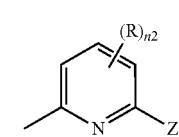

(4)

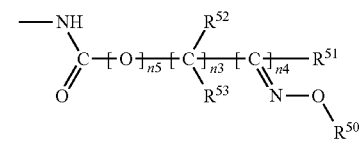

(a)

4 Claims, No Drawings

TETRAZOLYL OXIME DERIVATIVE, SALT THEREOF, AND PLANT DISEASE CONTROL AGENT

TECHNICAL FIELD

The present invention relates to a tetrazolyl oxime derivative or salt thereof, and a plant disease control agent containing the same as an active ingredient.

Priority is claimed on Japanese Patent Application No. 2009-047770, filed Mar. 2, 2009, the content of which is incorporated herein by reference.

BACKGROUND ART

Until now, in the cultivation of agricultural and horticultural crops, a large number of disease control agents are used against crop disease. For example, Patent documents 1-6 disclose a tetrazolyl oxime derivative having a structure similar to the compound of the present invention.

However, since the control effects of the conventional plant disease control agents may be inadequate, the use thereof may be restricted due to the appearance of agrichemical-resistant pathogenic organisms, and plants may be damaged or contaminated by the agrichemical or the agrichemical may demonstrate toxicity to humans, livestock or marine life, a considerable number of these disease control agents are not considered to be satisfactory. Thus, there is a need to develop a plant disease control agent that can be used safely and has few of these shortcomings.

PRIOR ART LITERATURE

Patent Document

Patent document 1: Japanese Unexamined Patent Application, First Publication No. 2004-131416
Patent document 2: Japanese Unexamined Patent Application, First Publication No. 2004-131392
Patent document 3: Japanese Unexamined Patent Application, First Publication No. 2003-137875
Patent document 4: WO 2008/006873
Patent document 5: WO 2008/006874
Patent document 6: WO 2008/006875

DISCLOSURE OF INVENTION

Problems to be Solved by the Invention

The present invention was conceived in view of the above-described circumstances encountered in the conventional art, and has as its objective the provision of a novel tetrazolyl oxime derivative or salt thereof, and a plant disease control agent containing at least one of the same as an active ingredient, which has excellent effects in controlling plant disease.

Means for Solving the Problems

The present inventors carried out exhaustive research on a number of syntheses of tetrazolyl oxime derivatives or salts thereof, as well as their physiological activities to solve the problems disclosed above, and completed the present invention with the discovery that a tetrazolyl oxime derivative represented by formula (1) or salt thereof has excellent control effect against plant disease, and has no chemical damage to useful plants.

Namely, the first aspect of the present invention is a tetrazoyl oxime derivative represented by formula (1) or salt thereof.

[Chemical formula 1]

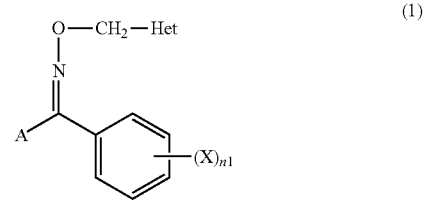

In formula (1), X represents a halogen atom, C1-8 alkyl group, C1-8 alkoxy group, cyano group, C1-8 alkyl sulfonyl group, nitro group, C1-8 haloalkyl group, or optionally substituted aryl group.

n1 represents an integer of 0 to 5. When n1 is 2 or more, plural X may be the same or different from each other.

A represents a tetrazolyl group represented by formula (2) or (3).

[Chemical formula 2]

In formula (2), Y represents a C1-8 alkyl group.

[Chemical formula 3]

In formula (3), Y is as defined above.

Het represents a pyridyl group represented by formula (4), or a thiazolyl group represented by formula (5).

[Chemical formula 4]

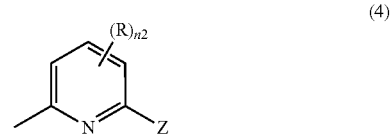

In formula (4), R represents a halogen atom, cyano group, nitro group, hydroxy group, thiol group, formyl group, carboxyl group, optionally substituted amino group, optionally substituted C1-8 alkyl group, optionally substituted C2-8 alkenyl group, optionally substituted C2-8 alkynyl group, optionally substituted aryl group, optionally substituted heterocyclic group, $OR^1$, $S(O)_m R^1$, $COR^1$, or $CO_2 R^1$. $R^1$ represents an optionally substituted amino group, optionally substituted C1-8 alkyl group, optionally substituted C3-8 cycloalkyl group, optionally substituted C2-8 alkenyl group, optionally substituted C2-8 alkynyl group, optionally substituted aryl group, or optionally substituted heterocyclic group.

m represents an integer of 0 to 2.

n2 represents an integer of 0 to 3. When n2 is 2 or more, plural R may be the same or different from each other.

Z represents a group represented by formula (a).

[Chemical formula 5]

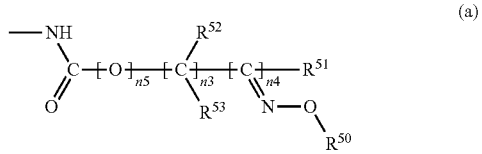

(a)

In formula (a), $R^{50}$ represents a hydrogen atom, optionally substituted C1-8 alkyl group, optionally substituted C2-8 alkenyl group, optionally substituted C2-8 alkynyl group, optionally substituted aryl group, optionally substituted heterocyclic group, optionally substituted aralkyl group, or optionally substituted heteroaralkyl group.

$R^{51}$ represents a hydrogen atom, optionally substituted C1-8 alkyl group, optionally substituted C2-8 alkenyl group, optionally substituted C2-8 alkynyl group, optionally substituted C1-8 alkoxy group, cyano group, optionally substituted acyl group, optionally substituted aryl group, optionally substituted heterocyclic group, optionally substituted aralkyl group, or optionally substituted heteroaralkyl group.

$R^{50}$ and $R^{51}$ may bond together to form a 5- to 8-membered ring.

$R^{52}$ represents a hydrogen atom, optionally substituted C1-8 alkyl group, optionally substituted C1-8 alkoxy group, or halogen atom.

$R^{53}$ represents a hydrogen atom, optionally substituted C1-8 alkyl group, optionally substituted C1-8 alkoxy group, or halogen atom.

n3 represents an integer of 0 to 2.

When n3 is 2, plural $R^{52}$ or $R^{53}$ may be the same or different from each other.

n4 represents 1 or 2.

When n4 is 2, plural $R^{50}$ may be the same or different from each other.

n5 represents 0 or 1.

[Chemical formula 6]

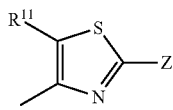

(5)

In formula (5), $R^{11}$ represents a hydrogen atom, halogen atom, cyano group, nitro group, hydroxy group, thiol group, formyl group, carboxyl group, optionally substituted amino group, optionally substituted C1-8 alkyl group, optionally substituted C2-8 alkenyl group, optionally substituted C2-8 alkynyl group, optionally substituted aryl group, optionally substituted heterocyclic group, $OR^1$, $S(O)_m R^1$, $COR^1$, or $CO_2 R^1$. $R^1$ and m are as defined above.

Z is as defined above.

In the present invention, n1 is preferably 0, and/or Y is preferably a methyl group in the tetrazolyl oxime derivative or salt thereof.

In addition, the second aspect of the present invention is a plant disease control agent containing the above-described tetrazolyl oxime derivative or salt thereof as an active ingredient.

In addition, in this description, "Ca-b XXX group" indicates that the group has a carbon number of a to b.

Effects of the Invention

The tetrazolyl oxime derivative or salt thereof of the present invention demonstrates superior control effects against plant disease at low doses, and eliminates concern over chemical damage to useful plants. Since the plant disease control agent of the present invention contains the tetrazolyl oxime derivative or salt thereof, it allows the plant disease control agent to be effective in controlling disease in cultivation of agricultural and horticultural crops, prevent chemical damages to crops and environmental contamination, and to reduce toxicity to humans, livestock or marine life.

BEST MODE FOR CARRYING OUT THE INVENTION

The following provides a detailed explanation of the present invention by dividing into sections describing 1) a tetrazolyl oxime derivative or salt thereof, and 2) a plant disease control agent.

1) Tetrazolyl Oxime Derivative or Salt Thereof

The tetrazolyl oxime derivative of the present invention is represented by the above-mentioned formula (1).

In formula (1), X represents a halogen atom, C1-8 alkyl group, C1-8 alkoxy group, cyano group, C1-8 alkyl sulfonyl group, nitro group, C1-8 haloalkyl group, or optionally substituted aryl group.

Examples of halogen atom include a fluorine atom, chlorine atom, bromine atom, and iodine atom.

Examples of the C1-8 alkyl group include a methyl group, ethyl group, n-propyl group, i-propyl group, n-butyl group, i-butyl group, s-butyl group, t-butyl group, n-pentyl group, n-hexyl group and the like.

Examples of the C1-8 alkoxy group include a methoxy group, ethoxy group, n-propoxy group, i-propoxy group, n-butoxy group, i-butoxy group, s-butoxy group, t-butoxy group, n-hexyloxy group and the like.

Examples of the C1-8 alkyl sulfonyl group include a methyl sulfonyl group, ethyl sulfonyl group, n-propyl sulfonyl group, i-propyl sulfonyl group, t-butyl sulfonyl group and the like.

Examples of the C1-8 haloalkyl group include a fluoromethyl group, chloromethyl group, bromomethyl group, difluoromethyl group, dichloromethyl group, trifluoromethyl group, trichloromethyl group, trifluoroethyl group, pentafluoroethyl group, 3,3,3,2,2-pentafluoropropyl group, 2,2,2-trifluoro-1-trifluoromethyl ethyl group and the like.

An aryl group means a monocyclic or polycyclic aryl group. In addition, if the polycyclic aryl group includes at least one aromatic ring, the other rings of the polycyclic aryl group may be a saturated ring, unsaturated ring or aromatic ring. Among the aryl groups, a C6-10 aryl group is preferable. Examples of the unsubstituted aryl group include a phenyl group, 1-naphthyl group, 2-naphthyl group, azulenyl group, indanyl group, tetralinyl group and the like.

The substituent of the substituted aryl group is not particularly limited as long as it is chemically acceptable. Specifically, the following substituents may be exemplified.

(1) halogen atoms such as a fluorine atom, chlorine atom, bromine atom or iodine atom; (2) alkyl groups such as a methyl group, ethyl group, n-propyl group, i-propyl group, n-butyl group, s-butyl group, i-butyl group, t-butyl group, n-pentyl group or n-hexyl group; (3) cycloalkyl groups such as a cyclopropyl group, cyclobutyl group, cyclopentyl group, cyclohexyl group or cycloheptyl group; (4) alkoxy groups such as a methoxy group, ethoxy group, n-propoxy group, isopropoxy group, n-butoxy group, i-butoxy group, s-butoxy group or t-butoxy group; (5) alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group;

(6) cycloalkenyl groups such as a 2-cyclopropenyl group, 2-cyclopentenyl group, 3-cyclohexenyl group or 4-cyclooctenyl group; (7) alkenyloxy groups such as a vinyloxy group, allyloxy group, 1-propenyloxy group or 2-butenyloxy group; (8) alkynyl groups such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group; (9) alkynyloxy groups such as an ethynyloxy group or propargyloxy group; (10) aryl groups such as a phenyl group, 1-napthyl group or 2-naphthyl group;

(11) aryloxy groups such as a phenoxy group or 1-naphthoxy group; (12) aralkyl groups such as a benzyl group or phenethyl group; (13) aralkyloxy groups such as a benzyloxy group or phenethyloxy group; (14) acyl groups such as a formyl group, acetyl group, propionyl group, benzoyl group, cyclohexylcarbonyl group, phthaloyl group, alkoxycarbonyl groups (such as a methoxycarbonyl group, ethoxycarbonyl group, n-propoxycarbonyl group, i-propoxycarbonyl group, n-butoxycarbonyl group, t-butoxycarbonyl group or the like), aminocarbonyl group (such as aminocarbonyl group, methyl aminocarbonyl group, diethyl aminocarbonyl group, phenyl aminocarbonyl group, benzyl aminocarbonyl group or the like) or the like; (16) carboxyl groups; (17) hydroxy groups; (18) haloalkyl groups such as a chloromethyl group, chloroethyl group, 1,2-dichloro-n-propyl group, 1-fluoro-n-butyl group or perfluoro-n-pentyl group; (19) haloalkoxy groups such as 2-chloro-n-propoxy group, or 2,3-dichlorobutoxy group, trifluoromethoxy group; (20) haloalkenyl groups such as a 2-chloro-1-propenyl group or 2-fluoro-1-butenyl group; (21) haloalkynyl groups such as a 4,4-dichloro-1-butynyl group, 4-fluoro-1-pentynyl group or 5-bromo-2-pentynyl group;

(22) haloalkenyloxy groups such as a 2-chloro-1-propenyloxy group or 3-bromo-2-butenyloxy group; (23) haloalkynyl groups such as a 3-chloro-propargyl group or 3-iodo-propargyl group; (24) haloalkynyloxy groups such as a 3-chloro-propargyloxy group or 3-iodo-propargyloxy group; (25) haloaryl groups such as a 4-chlorophenyl group, 4-fluorophenyl group or 2,4-dichlorophenyl group; (26) haloaryloxy groups such as, a 4-fluorophenoxy group or 4-chloro-1-naphthoxy group; (27) halogen-substituted acyl groups such as a chloroacetyl group, trifluoroacetyl group, trichloroacetyl group or 4-chlorobenzoyl group; (28) alkoxyalkyl groups such as a methoxymethyl group, ethoxymethyl group, 1-ethoxyethyl group or 2-ethoxyethyl group; (29) alkoxyalkoxy groups such as a methoxymethoxy group, ethoxymethoxy group, 1-ethoxyethoxy group or 2-ethoxyethoxy group; (30) cyano groups;

(31) isocyano groups; (32) nitro groups; (33) isocyanato groups; (34) cyanato groups; (35) amino groups ($NH_2$); (36) alkylamino groups such as a methylamino group, dimethylamino group or diethylamino group; (37) acylamino groups such as an anilino group, naphthylamino group or anthranylamino group; (38) aralkylamino groups such as a benzylamino group or phenethylamino group; (39) alkylsulfonylamino groups such as a methylsulfonylamino group, ethylsulfonylamino group, n-propylsulfonylamino group, i-propylsulfonylamino group or n-butylsulfonylamino group; (40) arylsulfonylamino groups such as a phenylsulfonylamino group;

(41) heteroarylsulfonylamino groups such as a piperazinylsulfonylamino group; (42) acylamino groups such as a formylamino group, acetylamino group, propanoylamino group, butyrylamino group, i-propylcarbonylamino group or benzoylamino group; (43) alkoxycarbonylamino groups such as a methoxycarbonylamino group or ethoxycarbonylamino group; (44) haloalkylsulfonylamino groups such as a fluoromethylsulfonylamino group, chloromethylsulfonylamino group, bromomethylsulfonylamino group, difluoromethylsulfonylamino group, dichloromethylsulfonylamino group, 1,1-difluoroethylsulfonylamino group, trifluoromethylsulfonylamino group, 2,2,2-trifluoroethylsulfonylamino group or pentafluoroethyl sulfonyl amino group; (45) bis(alkylsulfonyl)amino groups such as a bis(methylsulfonyl)amino group, bis(ethylsulfonyl)amino group, (ethylsulfonyl)(methylsulfonyl)amino group, bis(n-propylsulfonyl)amino group, bis(i-propylsulfonyl)amino group, bis(n-butylsulfonyl)amino group or bis(t-butylsulfonyl)amino group;

(46) bis(haloalkylsulfonyl)amino groups such as a bis(fluoromethylsulfonyl)amino group, bis(chloromethylsulfonyl)amino group, bis(bromomethylsulfonyl)amino group, bis(dichloromethylsulfonyl)amino group, bis(1,1-difluoroethylsulfonyl)amino group, bis(trifluoromethylsulfonyl)amino group, bis(2,2,2-trifluoroethylsulfonyl)amino group or bis(pentafluoroethylsulfonyl)amino group; (47) optionally substituted hydrazino groups such as a hydrazino group, N'-phenylhydrazino group, N'-methoxycarbonylhydrazino group, N'-acetylhydrazino group or N-methylhydrazino group; (48) optionally substituted aminocarbonyl groups such as an aminocarbonyl group, dimethylaminocarbonyl group, phenylaminocarbonyl group or N-phenyl-N-methylaminocarbonyl group; (49) optionally substituted hydrazinocarbonyl groups such as a hydrazinocarbonyl group, N'-methylhydrazinocarbonyl group or N'-phenylhydrazinocarbonyl group; (50) optionally substituted iminoalkyl groups such as an N-methyliminomethyl group, 1-N-phenyliminoethyl group, N-hydroxyiminomethyl group or N-methoxyiminomethyl group;

(51) thiol groups; (52) isothiocyanato groups; (53) thiocyanato groups; (54) alkylthio groups such as a methylthio group, ethylthio group, n-propylthio group, isopropylthio group, n-butylthio group, isobutylthio group, s-butylthio group or t-butylthio group; (55) alkenylthio groups such as a vinylthio group or allylthio group; (56) alkynylthio groups such as an ethynylthio group or propargylthio group; (57) arylthio groups such as a phenylthio group or naphthylthio group; (58) heteroarylthio groups such as a 2-piridylthio group or 3-pyridazylthio group; (59) aralkylthio groups such as a benzylthio group or phenethylthio group; (60) heteroaralkylthio groups such as a 2-pyridylmethylthio group or 2-furylmethylthio group; (61) alkylthiocarbonyl groups such as a methylthiocarbonyl group, ethylthiocarbonyl group, n-propylthiocarbonyl group, isopropylthiocarbonyl group, n-butylthiocarbonyl group, isobutylthiocarbonyl group, s-butylthiocarbonyl group or t-butylthiocarbonyl group;

(62) alkylthioalkyl groups such as a methylthiomethyl group or 1-methylthioethyl group; (63) arylthioalkyl groups such as a phenylthiomethyl group or 1-phenylthioethyl group; (64) alkylthioalkoxy groups such as a methylthiomethoxy group or 1-methylthioethoxy group; (65) arylthioalkoxy groups such as a phenylthiomethoxy group or 1-phenylthioethoxy group; (66) alkylsulfonyl groups such as a methylsulfinyl group, ethylsulfinyl group or t-butylsulfinyl group; (67) alkenylsulfinyl groups such as an allylsulfinyl group; (68) alkynylsulfinyl groups such as a propargylsulfinyl group; (69) arylsulfinyl groups such as a phenylsulfinyl group; (70) heteroarylsulfinyl groups such as a 2-pyridylsulfinyl group or 3-pyridylsulfinyl group; (71) aralkylsulfinyl groups such as a benzylsulfinyl group or phenethylsulfinyl group; (72) heteroarylalkylsulfinyl groups such as a 2-pyridylmethylsulfinyl group or 3-pyridylmethylsulfinyl group;

(73) alkylsulfonyl groups such as a methylsulfonyl group, ethylsulfonyl group or t-butylsulfonyl group; (74) alkenylsulfonyl groups such as an allylsulfonyl group; (75) alkynylsulfonyl groups such as a propargylsulfonyl group; (76) arylsulfonyl groups such as a phenylsulfonyl group; (77) heteroarylsulfonyl groups such as a 2-pyridylsulfonyl group or 3-pyridylsulfonyl group; (78) aralkylsulfonyl groups such as a benzylsulfonyl group or phenethylsulfonyl group; (79) heteroarylalkylsulfonyl groups such as a 2-pyridylmethylsulfonyl group or 3-pyridylmethylsulfonyl group; (80) unsaturated heterocyclic 5-membered ring groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group or 1,2,4-triazol-5-yl group;

(81) unsaturated heterocyclic 6-membered ring groups such as a pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-5-yl group, 1,3,5-triazin-2-yl group or 1,2,4-triazin-3-yl group; (82) saturated or partially unsaturated heterocyclic groups such as a tetrahydrofuran-2-yl group, tetrahydropyran-4-yl group, piperidin-3-yl group, pyrrolidin-2-yl group, morpholino group, piperidino group, N-methylpiperazino group or oxazolin-2-yl group; (83) heterocyclooxy groups such as a 2-pyridyloxy group or 3-isoxazolyloxy group; (84) heteroarylalkyl groups such as a 2-pyridylmethyl group or 3-pyridylmethyl group; (85) heteroarylalkoxy groups such as a 2-pyridylmethoxy group or 3-pyridylmethoxy group. These substituents exemplified in (1) to (85) above may also have substituents exemplified in (1) to (85) as long as it is chemically acceptable.

Examples of the substituted aryl group include a 4-fluorophenyl group, 4-chlorophenyl group, 2,4-dichlorophenyl group, 3,4-dichlorophenyl group, 3,5-dichlorophenyl group, 2,6-difluorophenyl group, 4-trifluoromethyl phenyl group, 4-methoxyphenyl group, 3,4-dimethoxyphenyl group, 3,4-methylene dioxyphenyl group, 4-trifluoromethoxyphenyl group, 4-methoxy-1-naphthyl group and the like.

Among these groups, X is preferably a halogen atom.

n1 represents an integer of 0 to 5, preferably an integer of 0 to 3, more preferably 0. In addition, when n1 is 2 or more, plural X may be the same or different from each other.

A represents a tetrazolyl group represented by formula (2) or (3). Among these groups, a tetrazolyl group represented by formula (2) is preferable.

In formulas (2) and (3), Y represents a C1-8 alkyl group. Examples of the C1-8 alkyl group include a methyl group, ethyl group, n-propyl group, i-propyl group, n-butyl group, i-butyl group, s-butyl group, t-butyl group, n-pentyl group, n-hexyl group and the like.

Among these groups, Y is preferably a C1-3 alkyl group, more preferably a methyl group.

Het represents a pyridyl group represented by formula (4), or a thiazolyl group represented by formula (5). Among these groups, a pyridyl group represented by formula (4) is preferable.

In formula (4), R represents a halogen atom, cyano group, nitro group, hydroxy group, thiol group, formyl group, carboxyl group, optionally substituted amino group, optionally substituted C1-8 alkyl group, optionally substituted C2-8 alkenyl group, optionally substituted C2-8 alkynyl group, optionally substituted aryl group, optionally substituted heterocyclic group, $OR^1$, $S(O)_m R^1$, $COR^1$, or $CO_2 R^1$.

Examples of the halogen atom, unsubstituted C1-8 alkyl group and optionally substituted aryl group represented as R include the same groups as the aforementioned examples of X.

Examples of the unsubstituted C2-8 alkenyl group represented as R include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group and the like.

Examples of the unsubstituted C2-8 alkynyl group represented as R include an ethynyl group, 1-propynyl group, 2-propynyl group, 1-butyryl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group and the like.

Examples of the unsubstituted heterocyclic group represented as R include unsaturated heterocyclic 5-membered ring groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group or 1,3,4-oxadiazol-2-yl group, 1,3,4-thiadiazol-2-yl group, 1,2,3-triazol-4-yl group, 1,2,4-triazol-3-yl group, 1,2,4-triazol-5-yl group or the like; unsaturated heterocyclic 6-membered ring group such as a pyridin-2-yl group, pyridin-3-yl group, pyridin-4-yl group, pyridazin-3-yl group, pyridazin-4-yl group, pyrazin-2-yl group, pyrimidin-5-yl group, 1,3,5-triazin-2-yl group, 1,2,4-triazin-3-yl group or the like; and saturated or partially unsaturated heterocyclic groups such as a tetrahydrofuran-2-yl group, tetrahydropyran-4-yl group, piperidin-3-yl group, pyrrolidin-2-yl group, morpholino group, piperidino group, piperazino group, N-methylpiperazino group, aziridino group, azetidino group, pyrrolidino group, oxazolin-2-yl group or the like; and the like.

Examples of the "substituent" of the substituted amino group, substituted C1-8 alkyl group, substituted C2-8 alkenyl group, substituted C2-8 alkynyl group and substituted heterocyclic group represented as R include the same "substituent" of the substituted aryl group exemplified for the aforementioned X, as long as it is chemically acceptable.

Examples of the substituted amino group include a methyl amino group, dimethyl amino group, methyl ethyl amino group, diethyl amino group, t-butoxycarbonyl methyl amino group, t-butoxycarbonyl amino group, acetyl methyl amino group, acetyl ethyl amino group, benzoyl methyl amino group and the like.

Examples of the substituted C1-8 alkyl group include a chloromethyl group, methoxymethyl group, methyl thiomethyl group, methyl sulfonyl methyl group, dimethyl aminomethyl group, trichloromethyl group, trifluoromethyl group, 2-chloroethyl group and the like.

Examples of the substituted C2-8 alkenyl group include a 2-chloroethenyl group, 2-fluoroethenyl group, 3,3,3-trifluoro-1-pentenyl group, 1,2,2-trifluoroethenyl group, 2,3,3-trifluoro-2-propenyl group, 2,3,3-triiodo-2-propenyl group, 2-methoxyethenyl group and the like.

Examples of the substituted C2-8 alkynyl group include a 2-chloroethynyl group, 2-fluoroethynyl group, 3-fluoro-1-propynyl group, 3,3,3-trifluoro-1-propynyl group, 3-fluoro-2-propynyl group, 3-iodo-2-propynyl group and the like.

Examples of the substituted heterocyclic group include a 3-trifluoromethyl pyridin-2-yl group, 4-trifluoromethoxy-2-pyridyl group, 3-methyl-1-pyrazolyl group, 4-trifluoromethyl-1-imidazolyl group, 3,4-difluoropyrrolidino group and the like.

$R^1$ of the groups of $OR^1$, $S(O)_mR^1$, $COR^1$ and $CO_2R^1$ that are represented as R represents an optionally substituted amino group, optionally substituted C1-8 alkyl group, optionally substituted C3-8 cycloalkyl group, optionally substituted C2-8 alkenyl group, optionally substituted C2-8 alkynyl group, optionally substituted aryl group, or optionally substituted heterocyclic group. In addition m represents an integer of 0 to 2.

Examples of the optionally substituted C1-8 alkyl group, optionally substituted C2-8 alkenyl group, optionally substituted C2-8 alkynyl group, optionally substituted aryl group, optionally substituted amino group and optionally substituted heterocyclic group, which are represented as $R^1$, include the same groups as the aforementioned examples of R.

Examples of the unsubstituted C3-8 cycloalkyl group include a cyclopropyl group, cyclobutyl group, cyclopentyl group, cyclohexyl group, cycloheptyl group and the like.

In addition, examples of the "substituent" of the substituted C3-8 cycloalkyl group represented as $R^1$ include the same groups as the aforementioned examples of the "substituent" of the substituted aryl group represented as X, as long as it is chemically acceptable.

Examples of $OR^1$ include a methoxy group, ethoxy group, n-propoxy group, i-propoxy group, n-butoxy group, s-butoxy group, i-butoxy group, t-butoxy group, methoxymethoxy group, ethoxymethoxy group, methoxyethoxy group, ethoxyethoxy group, vinyloxy group, 1-propenyloxy group, 2-propenyloxy group, ethynyloxy group, 1-propynyloxy group, 2-propynyloxy group, aminooxy group, methyl aminooxy group, diethyl aminooxy group, methoxycarbonyl aminooxy group, phenoxy group, trichloromethoxy group, trifluoromethoxy group, difluoromethoxy group, 2,2,2-trifluoroethoxy group, pentafluoroethoxy group, 2-fluoroethoxy group and the like.

Examples of $S(O)_mR^1$ include a dimethyl aminothio group, chloromethyl thio group, 3-butenyl thio group, ethynyl thio group, 3-methyl phenyl thio group, methyl sulfinyl group, ethyl sulfinyl group, 1-butenyl sulfinyl group, 1-hexynyl sulfinyl group, 2,3-dimethyl phenyl sulfinyl group, methyl sulfonyl group, dimethyl aminosulfonyl group, N-ethyl-N-methyl aminosulfonyl group, n-hexyl sulfonyl group, 2-methyl-2-butenyl sulfonyl group, 2-propynyl sulfonyl group, 2-naphthyl sulfonyl group, phenyl sulfonyl group, 2-nitrophenyl sulfonyl group, p-tolyl sulfonyl group and the like.

Examples of $COR^1$ include an acetyl group, benzoyl group, propanoyl group, i-propyl carbonyl group, t-butyl carbonyl group, cyclopropyl carbonyl group, cyclobutyl carbonyl group, cyclopentyl carbonyl group, vinyl carbonyl group, 1-propenyl carbonyl group, 2-propenyl carbonyl group, i-propenyl carbonyl group, 1-propynyl carbonyl group, 2-propynyl carbonyl group, 3-butenyl carbonyl group, methyl aminocarbonyl group, dimethyl aminocarbonyl group, N-methyl-N-ethyl aminocarbonyl group, aziridinocarbonyl group, azetidinocarbonyl group, pyrrolidinocarbonyl group, piperidinocarbonyl group, morpholinocarbonyl group, piperazinocarbonyl group, N-methyl piperazinocarbonyl group and the like.

Examples of $CO_2R^1$ include a methoxycarbonyl group, trifluoromethoxycarbonyl group, 1-pentenyloxycarbonyl group, 2-propynyloxycarbonyl group, phenoxycarbonyl group and the like.

Among these groups, R is preferably a halogen atom, optionally substituted amino group, C1-8 alkyl group, $OR^1$, and $SR^1$, and more preferably an optionally substituted amino group, C1-8 alkyl group, $OR^1$, and $SR^1$.

The optionally substituted amino group is preferably an amino group ($NH_2$ group) and a dialkyl amino group, and the C1-8 alkyl group is preferably a C1-4 alkyl group, and $OR^1$ is preferably a C1-4 alkoxy group, and $SR^1$ is preferably a C1-4 alkyl thio group.

n2 represents an integer of 0 to 3. n2 is preferably 0. When n2 is 2 or more, plural R may be the same or different from each other.

In formula (5), $R^{11}$ represents a hydrogen atom, halogen atom, cyano group, nitro group, hydroxy group, thiol group, formyl group, carboxyl group, optionally substituted amino group, optionally substituted C1-8 alkyl group, optionally substituted C2-8 alkenyl group, optionally substituted C2-8 alkynyl group, optionally substituted aryl group, optionally substituted heterocyclic group, $OR^1$, $S(O)_mR^1$, $COR^1$, or $CO_2R^1$, and $R^1$ and m are as defined above.

Examples of the halogen atom, optionally substituted amino group, optionally substituted C1-8 alkyl group, optionally substituted C2-8 alkenyl group, optionally substituted C2-8 alkynyl group, optionally substituted aryl group, optionally substituted heterocyclic group, $OR^1$, $S(O)_mR^1$, $COR^1$ and $CO_2R^1$ represented as $R^{11}$ include the same groups as the examples of R.

In formulas (4) and (5), Z represents a group represented by formula (a).

In formula (a), $R^{50}$ represents a hydrogen atom, optionally substituted C1-8 alkyl group, optionally substituted C2-8 alkenyl group, optionally substituted C2-8 alkynyl group, optionally substituted aryl group, optionally substituted heterocyclic group, optionally substituted aralkyl group, or optionally substituted heteroaralkyl group.

$R^{51}$ represents a hydrogen atom, optionally substituted C1-8 alkyl group, optionally substituted C2-8 alkenyl group, optionally substituted C2-8 alkynyl group, optionally substituted C1-8 alkoxy group, cyano group, optionally substituted acyl group, optionally substituted aryl group, optionally substituted heterocyclic group, optionally substituted aralkyl group, or optionally substituted heteroaralkyl group.

$R^{50}$ and $R^{51}$ may bond together to form a 5- to 8-membered ring.

In formula (a), $R^{52}$ represents a hydrogen atom, optionally substituted C1-8 alkyl group, optionally substituted C1-8 alkoxy group, or halogen atom.

$R^{53}$ represents a hydrogen atom, optionally substituted C1-8 alkyl group, optionally substituted C1-8 alkoxy group, or halogen atom.

n3 represents an integer of 0 to 2.

When n3 is 2 or more, plural R5 or $R^{53}$ may be the same or different from each other.

n4 represents 1 or 2.

When n4 is 2, plural $R^{50}$ may be the same or different from each other.

n5 represents 0 or 1.

Examples of the unsubstituted aralkyl group of $R^{50}$ and $R^{51}$ include a benzyl group, phenethyl group and the like.

Examples of the unsubstituted heteroaralkyl group of $R^{50}$ and $R^{51}$ include 2-pyridyl methyl group, 3-pyridyl ethyl group and the like.

Examples of the optionally substituted acyl group of $R^{51}$ include a formyl group, acetyl group, benzoyl group, trifluoromethyl carbonyl group and the like.

Examples of the groups represented by $R^{50}$-$R^{53}$ include the same groups as the aforementioned examples of groups.

Examples of the "substitutent" in formula (a) include the same groups as the examples of the "substituent" of the substituted aryl group represented as X, as long as it is chemically acceptable.

Examples of the substituted aralkyl group of $R^{50}$ and $R^{51}$ include a 4-fluorobenzyl group, 3,5-dimethyl benzyl group and the like.

Examples of the substituted heteroaralkyl group of $R^{50}$ and $R^{51}$ include a (5-trifluoromethyl-2-pyridyl)methyl group and the like.

Since Z represents a group represented by formula (a), the tetrazolyl oxime derivative of the present invention demonstrates a superior plant disease control effect that has not been available in the conventional tetrazolyl oxime derivatives. Although the detail reasons are unknown, it is assumed that the moiety of ">C=N—$OR^{50}$" may provide some effects.

In the tetrazolyl oxime derivative represented by the aforementioned formula (1), there exists (E)-form and (Z)-form stereoisomers based on a carbon-nitrogen double bond of oxime moiety. These two stereoisomers along with mixtures thereof are also included in the present invention. Synthetic products are normally obtained in the form of the (Z)-form only or as a mixture of the (E)-form and (Z)-form. The two isomers can be respectively isolated from a mixture of the (E)-form and (Z)-form by separating in accordance with known techniques such as silica gel column chromatography. Both (Z)-form and (E)-form have activity, and (Z)-form is preferable.

The salt of the tetrazolyl oxime derivative of the present invention is a salt of a compound represented by formula (1).

There are no particular limitations provided they are agriculturally and horticulturally acceptable salts. Examples of the salt include salts of inorganic acids such as hydrochlorides, nitrates, sulfates phosphates or the like; and salts of organic acids such as acetates, lactates, propionates, benzoates or the like.

(Production Process of Tetrazolyl Oxime Derivative and Salt Thereof)

The tetrazolyl oxime derivative represented by formula (1) may be produced, for example, according to the method described in the publication of JP 2003-137875 or WO 03/016303.

[Chemical formula 7]

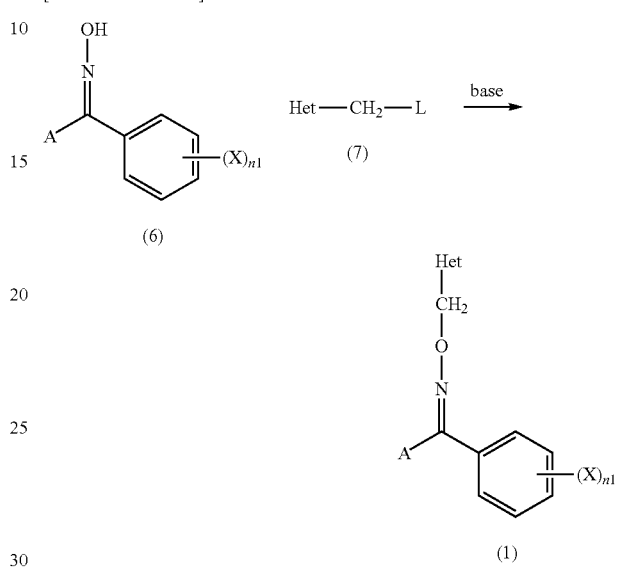

In formulas (1), (6) and (7), A, X, Het and n1 are as defined above, and L represents an elimination group such as a halogen atom.

Namely, the tetrazolyl oxime derivative of the present invention may be obtained by reacting an oxime represented by formula (6) with a compound represented by formula (7) in the presence of a base.

Examples of the base used in this reaction include inorganic bases such as sodium hydroxide, potassium hydroxide, sodium hydride, sodium carbonate, potassium carbonate or the like; and, organic bases such as triethylamine, 4-(dimethylamino) pyridine, pyridine, 1,8-diazabicyclo[5.4.0]undecene-7, 1,5-diazabicyclo[4.3.0]nonene-5 or the like.

One type of these bases can be used alone or two or more types can be used in combination.

The amount of base used is normally 0.01 to 100 times moles, and preferably 0.1 to 5 times moles with respect to the amount of the oxime represented by formula (6).

This reaction can be carried out in the presence or absence of a solvent.

There are no particular limitations on the solvent used provided it is an inert solvent in the reaction. Examples of solvents include hydrocarbon-based solvents such as pentane, hexane, heptane, benzene, toluene or xylene; halogen-based solvents such as dichloromethane, chloroform, carbon tetrachloride; nitrile-based solvents such as acetonitrile or propionitrile; ether-based solvents such as diethyl ether, dioxane or tetrahydrofuran; amide-based solvents such as N,N-dimethylformamide, N,N-dimethylacetamide or N-methylpyrrolidone; sulfoxide-based solvents such as dimethylsulfoxide; water; and mixed solvents thereof.

The temperature during the reaction is normally −70 to +200° C., and preferably −20 to +100° C.

Although the reaction time varies according to the reaction scale and the like, it is normally within the range of 30 minutes to 24 hours.

In addition, a salt of a compound represented by formula (1) can be produced allowing an acid to act on a compound represented by formula (1) in accordance with ordinary methods.

If Het represents a pyridyl group represented by formula (4) or a thiazolyl group represented by formula (5) in the compound represented by formula (7), the compound represented by formula (1) of the present invention may be directly obtained by the above-described reaction.

The tetrazolyl oxime derivative or salt there of the present invention may be produced by carrying out the reaction in the same manner described above using the compound represented by formula (8) or (9) instead of the compound represented by formula (7) to obtain a compound in which an amino-substituted pyridine group or amino-substituted thiazolyl group is introduced, and then substituting the amino group with the aforementioned Z. In addition, in formula (8) or (9), $R^{40}$ and $R^{41}$ represent a substituent such as a hydrogen atom, alkyl group or the like.

[Chemical formula 8]

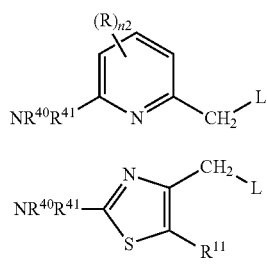

(8)

(9)

Examples of method substituting an amino group ($NR^{40}R^{41}$) with the aforementioned Z include (1) reacting the amino group with an oxocarboxylic acid ($R^{51}$—C(=O)—COOH, $R^{51}$—C(=O)—$R^c$COOH or the like) such as pyruvic acid or the like to convert into a group represented by $R^{51}$—C(=O)—C(=O)—NH—, $R^{51}$—C(=O)—$R^c$COOH or the like, and then reacting this group with O-alkyl hydroxylamine hydrochloride or the like; (2) reacting the amino group with an alkoxyiminocarboxylate ($R^{51}$—C(=N—$OR^{50}$)—$COOR^b$, $R^{51}$—C(=N—$OR^{50}$)—$R^d COOR^e$ or the like); or the like. In addition, alkoxyiminocarboxylate may be synthesized, for example, by reacting oxocarboxylate ($R^{51}$—C(=O)—$COOR^b$, $R^{51}$—C(=O)—$R^d COOR^e$ or the like) with hydroxylammonium chloride to obtain hydroxyiminocarboxylate, and then reacting it with alkyl halide ($R^{50}Xa$). In addition, here, $R^b$, $R^c$ and $R^e$ represent a hydrocarbon group, Xa represents a halogen atom. R4 represents —$[CR^{52}R^{53}]_{n3}$—.

In either of these reactions, the target compound represented by formula (1) and salt thereof can be isolated by carrying out an ordinary post-treatment operation following completion of the reaction. In addition, if purification of the product is required, known, commonly used purification means can be employed such as distillation, recrystallization or column chromatography.

A tetrazolyl oxime derivative or salt thereof represented by formula (1) (to be referred to as a "compound of the present invention") has superior antimicrobial effects against a wide spectrum of types of mold fungi such as *Oomycetes* species, *Ascomycetes* species, *Deuteromycetes* species and *Basidiomycetes* species.

Thus, a composition having as an active ingredient thereof a compound of the present invention can be used to control various plant diseases occurring during cultivation of agricultural and horticultural crops such as flowering plants, grasses and forage grasses by seed treatment, foliar spraying, soil application or paddy water application and the like.

Examples of crops in which plant diseases can be controlled along with their pathogen include:

Beets: Cercospora leaf spot (*Cercospora beticola*), Aphanomyces root rot (*Aphanomyces cochlioides*);

Peanuts: Brown leaf spot (*Mycosphaerella arachidis*), Leaf spot (*Mycosphaerella berkeleyi*);

Cucumbers: Powdery mildew (*Sphaerotheca fuliginea*), Gummy stem blight (*Mycosphaerella melonis*), Stem rot (*Sclerotinia sclerotiorum*), Gray mold (*Botrytis cinerea*), Scab (*Cladosporium cucumerinum*), Downy mildew (*Pseudoperonospora cubensis*);

Tomatoes: Gray mold (*Botrytis cinerea*), Leaf mold (*Cladosporium fulvum*), Cottony leak (*Phythium aphanidermatum*), Late blight (*Phytophthora infestans*);

Eggplants: Gray mold (*Botrytis cinerea*), Black rot (*Corynespora melongenae*), Powdery mildew (*Erysiphe cichoracearum*);

Spinach: Damping-off (*Pythium ultimum*),

Strawberries: Gray mold (*Botrytis cinerea*), Powdery mildew (*Sphaerotheca aphanis*);

Onions: Neck rot (*Botrytis allii*), Gray mold (*Botrytis cinerea*);

Kidney beans: Stem rot (*Sclerotinia sclerotiorum*), Gray mold (*Botrytis cinerea*);

Apples: Powdery mildew (*Podosphaera leucotricha*), Scab (*Venturia inaequalis*), Blossom blight (*Monilinia mali*);

Persimmons: Powdery mildew (*Phyllactinia kakicola*), Anthracnose (*Gloeosporium kaki*), Angular leaf spot (*Cercospora kaki*);

Peaches and cherries: Brown rot (*Monilinia fructicola*);

Grapes: Gray mold (*Botrytis cinerea*), Powdery mildew (*Uncinula necator*), Ripe rot (*Glomerella cingulata*), Downy mildew (*Plasmopara viticola*);

Pears: Scab (*Venturia nashicola*), Rust (*Gymnosporangium asiaticum*), Black spot disease (*Alternaria kikuchiana*);

Tea: Gray blight (*Pestalotia theae*), Anthracnose (*Collectotrichum theae-sinensi*);

Citrus: Scab (*Elsinoe fawcetti*), Blue mold (*Penicillium italicum*), Green mold (*Penicillium digitatum*), Gray mold (*Botrytis cinerea*);

Barley: Powdery mildew (*Erysiphe graminis* f sp. *hordei*), Loose smut (*Ustilago nuda*);

Wheat: Scab (*Gibberella zeae*), Rust (*Puccinia recondita*), Spot blotch (*Cochliobolus sativus*), Glume blotch (*Leptosphaeria nodorum*), Eye spot (*Pseudocercosporella herpotrichoides*); Powdery mildew (*Erysiphe graminis* f sp. *tritici*), Fusarium snow mold (*Micronectriella nivalis*), Browning root rot (*Pythium iwayamai*);

Rice: Blast (*Pyricularia oryzae*), Sheath blight (*Rhizoctonia solani*), Bakanae disease (*Gibberella fujikuroi*), Brown spot (*Cochliobolus niyabeanus*), Seedling blight (*Pythium graminicola*);

Soybeans: Purple blotch (*Cercospora kikuchii*), Downy mildew (*Peronospora manshurica*), Phytophthora rot (*Phytophthora sojae*);

Potatoes: Late blight (*Phytophthora infestans*), Clubroot (*Plasmodiophora brassicae*);

Tobacco: Sclerotinia stem-rot (*Sclerotinia sclerotiorum*), Powdery mildew (*Erysiphe cichoracearum*);

Tulips: Gray mold (*Botrytis cinerea*);

Bentgrass: *Sclerotinia* snow blight (*Sclerotinia borealis*), *Pythium* red blight (*Pythium aphanidermatum*);
Orchardgrass: Powdery mildew (*Erysiphe graminis*);

In addition, various pathogens have recently developed resistance to phenylamide fungicides and strobilurin fungicides resulting in inadequate efficacy of these fungicides, thereby creating the need for effective fungicides against resistant organisms as well. The compounds of the present invention also have superior antimicrobial effects against resistant organisms in addition to pathogens that are sensitive to these fungicides.

For example, the compounds of the present invention are effective against potato and tomato late blight (*Phytophthora infestans*), cucumber downy mildew (*Pseudoperonospora cubensis*) and grape downy mildew (*Plasmopara viticola*), which are resistant to metalaxyl, as well as sensitive organisms.

Moreover, the compounds of the present invention are effective against cucumber downy mildew (*Pseudoperonospora cubensis*) and grape downy mildew (*Plasmopara viticola*), which demonstrate resistance to strobilurin fungicides (such as kresoxim-methyl or azoxystrobin), as well as sensitive organisms.

Examples of diseases for which application is preferable include numerous types of diseases caused by *Oomycetes* species, such as grape downy mildew (*Plasmopara viticola*), cucubitaceous downy mildew (*Pseudoperonospora cubensis*), potato and tomato late blight (*Phytophthora infestans*), turf *Pythium* red blight (*Pythium aphanidermatum*) or beet black root disease (*Aphanomyces cochlioides*).

The compounds of the present invention can also be used as anti-fouling agents for preventing aquatic organisms from adhering to boat bottoms, fishing nets and other objects in contact with water.

In addition, some intermediate compounds produced in the production process of the compounds of the present invention also demonstrate antimicrobial activity.

Moreover, the compounds of the present invention can also be used as antimicrobial or anti-mold agents for walls, bathtubs, shoes or clothing by incorporating in paint or fibers and the like.

2) Plant Disease Control Agent

The plant disease control agent of the present invention contains as an active ingredient thereof at least one type of the compound of the present invention.

The plant disease control agent of the present invention may adopt a form containing only the compound of the present invention, or may adopt a form able to be adopted by ordinary agricultural chemicals, namely a wettable powder, granules, powder, emulsion, aqueous solution, suspension or flowable agent.

Examples of additives and/or carriers able to be added to the plant disease control agent used for the purpose of solid agents include botanical powders such as soybean powder or wheat powder, mineral fine powders such as diatomaceous earth, apatite, gypsum, talc, bentonite, pyrophyllite or clay, and organic and inorganic compounds such as sodium benzoate, urea or sodium sulfate.

In addition, examples of additives when intending to produce a liquid formulation include petroleum residues such as kerosene, xylene and solvent naphtha, and solvents such a cyclohexane, cyclohexanone, dimethylformamide, dimethylsulfoxide, alcohol, acetone, trichloroethylene, methyl isobutyl ketone, mineral oil, vegetable oil, water and the like.

Moreover, in the plant disease control agent of the present invention, a surfactant can be added in these preparations as necessary to obtain a uniform and stable form.

Examples of surfactants used include nonionic surfactants such as polyoxyethylene-alkyl phenyl ethers, polyoxyethylene-alkyl ethers, polyoxyethylene-higher fatty acid esters, polyoxyethylene-sorbitan fatty acid esters or polyoxyethylene-tristyryl phenyl ether; and sulfuric acid ester salts of polyoxyethylene-alkyl phenyl ethers, alkyl benzene sulfonates, sulfuric acid ester salts of higher alcohols, alkyl naphthalene sulfonates, polycarboxylates, lignin sulfonates, formaldehyde condensates of alkyl naphthalene sulfonates, and isobutylene-maleic anhydrate copolymer.

Although the amount of active ingredient in the preparations is not particularly limited, normally, it is 0.5 to 95% by mass, and preferably 2 to 70% by mass based on the total amount of the composition (preparation).

In the case the plant disease control agent of the present invention is a wettable powder, emulsion or flowable agent, it can be used in the form of a suspension or emulsion by diluting to a prescribed concentration with water. In addition, in the case it is in the form of a powder of granules, it can be used by spraying directly onto plants.

Although a compound of the present invention or plant disease control agent of the present invention is naturally adequately effective even if used alone, it can also be used by mixing with one or more types of various fungicides, insecticides, miticides or synergists.

Typical examples of fungicides, insecticides, miticides and plant growth regulators able to be used by mixing with a compound of the present invention or plant disease control agent of the present invention are indicated below.

(Fungicides)
Copper agents: basic copper chloride, basic copper sulfate or the like;
Sulfur agents: thiuram, zineb, maneb, mancozeb, ziram, propineb, polycarbamate;
Polyhaloalkylthio agents: captan, folpet, dichlorofluranid or the like;
Organic chlorine agents: chlorothalonil, fthalide or the like;
Organic phosphorous agents: IBP, EDDP, triclofos-methyl, pyrazophos, fosetyl;
Benzimidazole agents: thiophanate-methyl, benomyl, carbendazim, thiabendazole;
Dicarboximide agents: iprodione, procymidone, vinclozoline, fluoroimide or the like;
Carboxyamide agents: oxycarboxin, mepronil, flutolanil, tecloftalum, trichlamide, pencycuron or the like;
Acylalanine agents: metalaxil, oxadixyl, furalaxyl or the like;
Strobilurin-based agents: azoxystrobin, kresoxim-methyl, pyraclostrobin, trifloxystrobin, pyribencarb, famoxadone, fenamidone or the like;
Anilinopyrimidine agents: mepanipyrim, pyrimethanil, cyprodinil or the like;
SBI agents: triadimefon, triadimenol, bitertanol, myclobutanil, hexaconazole, propiconazole, triflumizole, procloraz, pefurazoate, fenarimol, pyrifenox, triforine, flusilazol, etaconazole, diclobutrazol, fluotrimazole, flutriafen, penconazole, diniconazole, imazalil, tridemorph, fenpropimorph, buthiobate, epoxyconazole, metconazole, prothioconazole, spiroxamine, fenhexamid, pyributicarb or the like;

Antibiotic agents: polyoxins, blasticidin-S, kasugamycin, validamycin, dihydrostreptomycin sulfate, etc. Anilide-based agents: boscalid, penthiopyrad, fluopyram, bixafen, etc. Guanidine-based agents: iminoctadine acetate salt, iminoctadine albesilate salt, dodine, guazatine, etc. Valine-based agents: dimethomorph, flumorph, iprovalicarb, benthiavalicarb, mandipropamid, etc.

Other antibiotic agents: cymoxanil, cyazofamid, amisulbrom, propamocarb, fluazinam, propamocarb acetate salt, ethaboxam, fluopicolide, zoxamide, cyflufenamid, metrafenone, proquinazid, hydroxy isoxazole, metasulfocarb, anilazine, isoprothiolane, ferimzone, probenazole, tiadinil, acibenzolar s-methyl, isotianil, pyroquilon, phthalide, tricyclazole, caxpropamid, fenoxanil, diclocymet, fluazinam, fludioxonil, pyrrolenitrine, hydroxyl isoxazole, flusulfamide, diethofencarb, quintozene, metasulfocarb, anilazine, quinomethionate, dithianon, dinocap, dichlomezine, oxolinic acid, lecithin, sodium bicarbonate, fenaminosulf, phenazine oxide, etc.

(Insecticides/Miticides)

Organic phosphorous and carbamate-based insecticides: fenthion, fenitrothion, diazinon, chiopyrifos, ESP, vamidothion, phenthoate, dimethoate, formothion, marathon, trichlorfon, thiometon, phosmet, dichlorphos, acephate, EPBP, methyl parathion, oxydemeton-methyl, ethion, salithion, cyanophos, isoxathion, pyridafenthion, phosalone, methidathion, sulprofos, chlorfenvinphos, tetrachlorvinphos, dimethylvinphos, propaphos, isofenphos, ethylthiometon, profenofos, pyraclofos, monocrotophos, azinphos-methyl, aldicarb, methomyl, thiodicarb, carbofuran, carbosulfan, benfuracarb, furathiocarb, propoxur, BPMC, MTMC, MIPC, carbaryl, pirimicarb, ethiofencarb, fenoxycarb or the like;

Pyrethroid insecticides: permethrin, dipermethrin, deltamethrin, fenvalerate, fenpropathrin, pyrethrin, allethrin, tetramethrin, resmethrin, dimethrin, propathrin, phenothrin, protolin, fluvalinate, cyfluthrin, cyhalothrin, flucythrinate, etofenprox, cycloprothin, tralomethrin, silafluofen, flufenprox, acrinathrin or the like;

Benzoylurea and other insecticides: diflubenzuron, chlorofluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotine sulfate, rotenone, metaldehyde, emamectin, flubendiamide, spinosad, machine oil, microbial agricultural drugs such as BT or insect pathogenic viruses or the like;

Nematicides:

Fenamiphos, fosthiazate or the like;

Miticides: Chlorobenzilate, phenisobromolate, dicofol, amitraz, BPPS, benzomate, hexythiazox, fenbutatinoxide, polynactin, quinomethionate, CPCBS, tetradifon, abamectin, milbemectin, clofentezine, cyhexatin, piridaben, fenpyroximate, tebufenpyrad, pyrimidifen, fenothiocarb, dienochlor, fluacrypyrim or the like;

(Plant Growth Regulators)

Gibberellin (such as gibberellin A3, gibberellin A4 or gibberellin A7), IAA, NAA or the like;

EXAMPLES

The present invention will be explained in more detail by way of Examples, but the present invention should not be interpreted to be limited to these Examples.

Example 1

Production of (Z)-(1-methyl-1H-tetrazol-5-yl)phenyl methanone-O-{2-[(1-methoxyimino)ethane carbonyl amino]pyridin-6-yl methyl}-oxime (Compound 1-a-3)

Step i

Production of (Z)-(1-methyl-1H-tetrazol-5-yl)phenyl methasone-O-[2-(acetyl carbonyl amino)pyridin-6-yl methyl]-oxime

[Chemical formula 9]

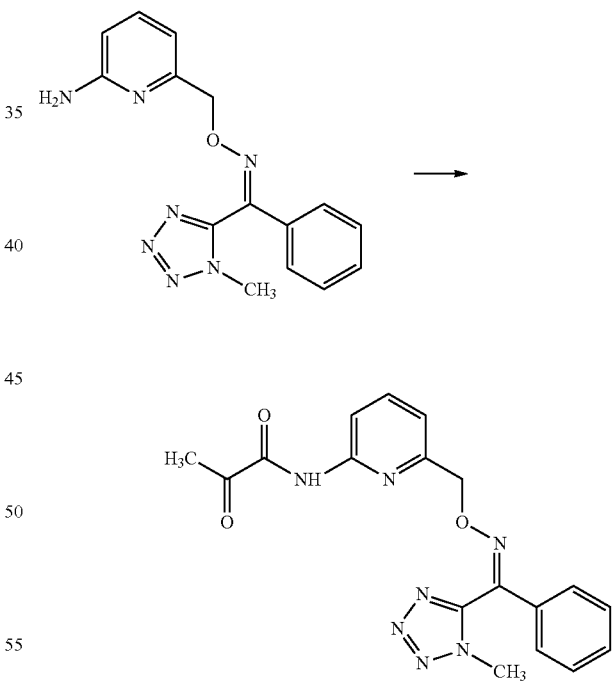

0.88 g (10.0 mmol) of pyruvic acid was dissolved in 20 ml of methylene chloride, and 1.21 g (10.0 mmol) of pivalic acid chloride and 1.06 g (10.5 mmol) of triethylamine were added to the resulting solution, followed by stirring for 30 minutes at room temperature. 0.31 g (1.0 mmol) of (Z)-(1-methyl-1H-tetrazol-5-yl)phenyl methanone-O-[2-aminopyridin-6-yl methyl]-oxime was added to the resulting solution, and stirred for one night at room temperature. The solvent was distilled off and the resulting residue was purified by silica gel column chromatography (eluent: hexane:ethyl acetate=4:1 (v/v)) to obtain 0.08 g of the target compound.

Step ii

Production of (Z)-(1-methyl-1H-tetrazol-5-yl)phenyl methanone-O-{2-[(1-methoxyimino)ethane carbonyl amino]pyridin-6-yl methyl}-oxime (Compound I-a-3)

[Chemical formula 10]

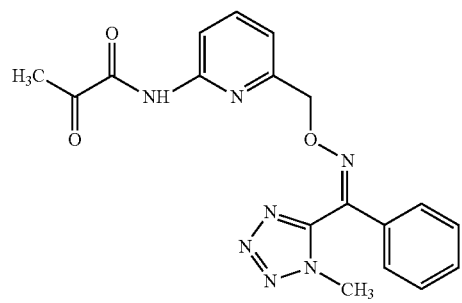

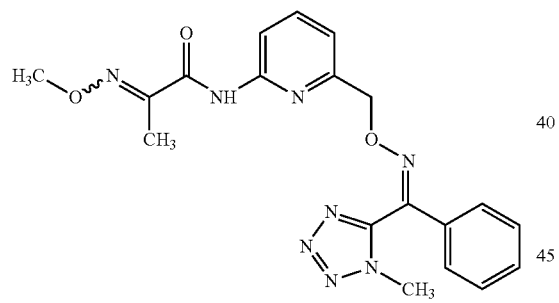

0.16 g (0.42 mmol) of (Z)-(1-methyl-1H-tetrazol-5-yl) phenyl methanone-O-[2-(acetyl carbonyl amino) pyridin-6-yl methyl]-oxime was dissolved in 10 ml of ethanol and 0.04 g (0.50 mmol) of O-methyl hydroxylamine hydrochloride was added to the resulting solution, followed by heating under reflux for 2.5 hours. Next, the solvent was distilled off under reduced pressure, neutralized with saturated sodium bicarbonate water, and extracted with ethyl acetate. The organic layer was dried by adding magnesium sulfate, and concentrated under reduced pressure. The resulting residue was purified by silica gel column chromatography (eluent: hexane:ethyl acetate=2:1 (v/v)) to obtain 0.09 g of the target compound.

The physical properties of compound 1-a-3 are as follows.

AMR;

$^1$H-NMR: 2.09 (s, 3H), 4.00 (s, 3H), 4.08 (s, 3H), 5.30 (s, 2H), 7.03 (d, 1H), 7.35-7.52 (m, 5H), 7.72 (t, 1H), 8.18 (d, 1H), 9.13 (br-s, 1H).

Example 2

Production of (Z)-(1-methyl-1H-tetrazol-5-yl)phenyl methanone-O-{2-[(1-n-propoxyimino)ethane carbonyl amino]pyridin-6-yl methyl}-oxime (Compound I-a-5)

Step i

Production of 2-hydroxyimino-propionic acid ethyl

[Chemical formula 11]

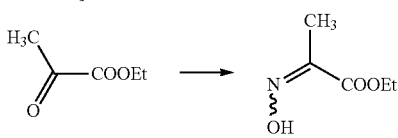

3.02 g (26.0 mmol) of pyruvic acid ethyl ester was dissolved in 30 ml of ethanol, and 1.90 g (27.3 mmol) of hydroxylammonium chloride was added to the resulting solution, followed by stirring for 80 minutes at room temperature. The solvent was distilled off under reduced pressure, and the resulting residue was dissolved in ethyl acetate, and washed with water and saturated brine. The organic layer was dried by adding magnesium sulfate, and concentrated under reduced pressure to obtain 3.08 g of the target compound.

Step ii

Production of 2-n-propoxyimino-propionic acid ethyl

[Chemical formula 12]

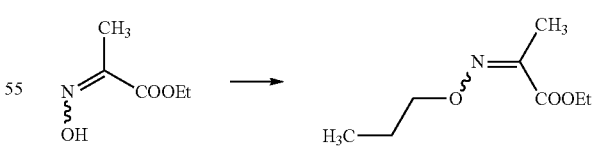

0.30 g (2.29 mmol) of 2-hydroxyimino-propionic acid ethyl ester and 0.56 g (4.58 mmol) of 1-bromopropane were dissolved in 5 ml of N,N-dimethyl formamide (DMF) and 0.63 g (4.58 mmol) of potassium carbonate was added to the resulting solution, followed by stirring for 2 hours at 100° C. Saturated ammonium chloride solution was added to the reaction solution, and extracted with ethyl acetate. The organic layer was washed with water and saturated brine, and dried by adding magnesium sulfate, and concentrated under reduced pressure to obtain 0.42 g of the target compound.

Step iii

Production of (Z)-(1-methyl-1H-tetrazol-5-yl)phenyl methanone-O-{2-[(1-n-propoxyimino)ethane carbonyl amino]pyridin-6-yl methyl}-oxime (Compound I-a-5)

[Chemical formula 13]

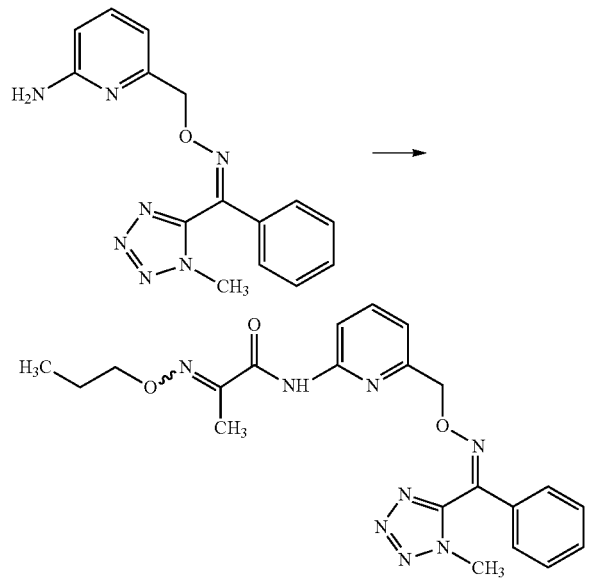

0.12 g (0.70 mmol) of 2-n-propoxyimino-propionic acid ethyl ester was dissolved in 2 ml of methanol and 0.035 g (0.91 mmol) of sodium hydroxide was added to the resulting solution, followed by stirring for 1 hour at room temperature. The solvent was distilled off under reduced pressure, and neutralized with 2N hydrochloric acid, and extracted with chloroform. The organic layer was dried by adding magnesium sulfate, and concentrated tinder reduced pressure to obtain a white solid substance. The white solid substance was dissolved in 5 ml of methylene chloride, and stirred for 40 minutes at room temperature after adding 0.11 g (0.84 mmol) of oxalyl chloride, and concentrated tinder reduced pressure. The residue was dissolved in 5 ml of methylene chloride and stirred for 1 hour at room temperature after adding 0.10 g (0.99 mmol) of triethylamine and 0.14 g (0.45 mmol) of (Z)-(1-methyl-1H-tetrazol-5-yl)phenyl methanone-O-[2-aminopyridin-6-yl methyl]-oxime. The solvent was distilled off and the resulting residue was purified by silica gel column chromatography (eluent: hexane:ethyl acetate=4:1 (v/v)) to obtain 0.10 g of the target compound.

The physical properties of compound 1-a-5 are as follows: VISC. OIL;
$^1$H-NMR: 0.99 (t, 3H), 1.76 (tq, 2H), 2.10 (s, 3H), 4.00 (s, 3H), 4.23 (t, 2H), 5.30 (s, 2H), 7.02 (d, 1H), 7.34-7.52 (m, 5H), 7.72 (t, 1H), 8.18 (d, 1H), 9.12 (br-s, 1H).

Example 3

Other examples of the tetrazolyl oxime derivatives of the present invention, which are produced by the above-described methods or the like, are shown in TABLES 1 to 5. TABLE 1 shows the examples of the compounds represented by formula (1-a). TABLE 2 shows the examples of the compounds represented by formula (1-b). TABLE 3 shows the examples of the compounds represented by formula (1-c). TABLE 4 shows the examples of the compounds represented by formula (1-d). TABLE 5 shows the examples of the compounds represented by formula (1-e). TABLE 6 shows the examples of the compounds represented by formula (1-f). TABLE 7 shows the examples of the compounds represented by formula (1-g).

In addition, these compounds are only some of the tetrazolyl oxime derivatives of the present invention. An ordinary skilled person can easily understand that other compounds which are not shown in this description, namely, the compounds which are substituted by various substituents complying with the purpose and scope of the present invention can also be obtained by the above-described method and can be used. In addition, the abbreviations described in the tables have the meanings as defined below: Me: Methyl, Et: Ethyl, n-Pr: normal propyl, i-Pr: isopropyl, c-Pr: cyclopropyl, Bn: benzyl, Ph: phenyl, Py: pyridine, THF: tetrahydrofuran, Boc: butoxycarbonyl, MeO: methoxy, EtO: Ethoxy, *: bonding position, *50: bonding position of $R^{50}$, *51: bonding position of $R^{51}$.

[Chemical formula 14]

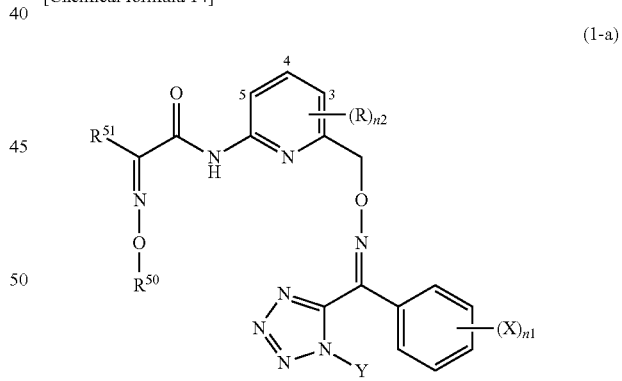

(1-a)

TABLE 1

| No. | $R^{50}$ | $R^{51}$ | $(R)_{n2}$ | $(X)_{n1}$ | Y | E/Z |
|---|---|---|---|---|---|---|
| 1-a-1 | H | H | — | — | Me | Z |
| 1-a-2 | H | Me | — | — | Me | Z |
| 1-a-3 | Me | Me | — | — | Me | Z |
| 1-a-4 | Et | Me | — | — | Me | Z |
| 1-a-5 | n-Pro | Me | — | — | Me | Z |
| 1-a-6 | CH$_2$CH=CH$_2$ | Me | — | — | Me | Z |
| 1-a-7 | CH$_2$CH=Cl$_2$ | Me | — | — | Me | Z |
| 1-a-8 | CH$_2$C≡CH | Me | — | — | Me | Z |

TABLE 1-continued

| No. | R⁵⁰ | R⁵¹ | (R)ₙ₂ | (X)ₙ₁ | Y | E/Z |
|---|---|---|---|---|---|---|
| 1-a-9 | CH₂CH₂OMe | Me | — | — | Me | Z |
| 1-a-10 | CH₂CF₃ | Me | — | — | Me | Z |
| 1-a-11 | CH₂CH₂CN | Me | — | — | Me | Z |
| 1-a-12 | Bn | Me | — | — | Me | Z |
| 1-a-13 | CH₂(Py-2-yl) | Me | — | — | Me | Z |
| 1-a-14 | Ph | Me | — | — | Me | Z |
| 1-a-15 | Py-2-yl | Me | — | — | Me | Z |
| 1-a-16 | Me | Ph | — | — | Me | Z |
| 1-a-17 | n-Pro | Ph | — | — | Me | Z |
| 1-a-18 | CH₂CH=CH₂ | Ph | — | — | Me | Z |
| 1-a-19 | CH₂C≡CH | Ph | — | — | Me | Z |
| 1-a-20 | CH₂CH₂OMe | Ph | — | — | Me | Z |
| 1-a-21 | Me | Py-2-yl | — | — | Me | Z |
| 1-a-22 | n-Pro | Py-2-yl | — | — | Me | Z |
| 1-a-23 | CH₂CH=CH₂ | Py-2-yl | — | — | Me | Z |
| 1-a-24 | CH₂C≡CH | Py-2-yl | — | — | Me | Z |
| 1-a-25 | CH₂CH₂OMe | Py-2-yl | — | — | Me | Z |
| 1-a-26 | Me | CH₂OMe | — | — | Me | Z |
| 1-a-27 | n-Pro | CH₂OMe | — | — | Me | Z |
| 1-a-28 | CH₂CH=CH₂ | CH₂OMe | — | — | Me | Z |
| 1-a-29 | CH₂C≡CH | CH₂OMe | — | — | Me | Z |
| 1-a-30 | CH₂CH₂OMe | CH₂OMe | — | — | Me | Z |
| 1-a-31 | Me | CF₃ | — | — | Me | Z |
| 1-a-32 | Me | CH₂CH=CH₂ | — | — | Me | Z |
| 1-a-33 | Me | CH₂C≡CH | — | — | Me | Z |
| 1-a-34 | Me | OMe | — | — | Me | Z |
| 1-a-35 | Me | CN | — | — | Me | Z |
| 1-a-36 | Me | Bn | — | — | Me | Z |
| 1-a-37 | Me | CH₂(Py-2-yl) | — | — | Me | Z |
| 1-a-38 | Me | Me | — | 2-F | Me | Z |
| 1-a-39 | Me | Me | — | 2-Me | Me | Z |
| 1-a-40 | Me | Me | — | 2-OMe | Me | Z |
| 1-a-41 | Me | Me | — | 2-CN | Me | Z |
| 1-a-42 | Me | Me | — | 2-SO₂Me | Me | Z |
| 1-a-43 | Me | Me | — | 2-NO₂ | Me | Z |
| 1-a-44 | Me | Me | — | 2-CF₃ | Me | Z |
| 1-a-45 | Me | Me | — | 2,4-F₂ | Me | Z |
| 1-a-46 | Me | Me | 3-F | — | Me | Z |
| 1-a-47 | Me | Me | 3-Me | — | Me | Z |
| 1-a-48 | Me | Me | 3-OMe | — | Me | Z |
| 1-a-49 | Me | Me | 3-CN | — | Me | Z |
| 1-a-50 | Me | Me | 3-SO₂Me | — | Me | Z |
| 1-a-51 | Me | Me | 3-NO₂ | — | Me | Z |
| 1-a-52 | Me | Me | 3-CF₃ | — | Me | Z |
| 1-a-53 | Me | Me | 3,4-F₂ | — | Me | Z |
| 1-a-54 | Me | Me | 3-OH | — | Me | Z |
| 1-a-55 | Me | Me | 3-SH | — | Me | Z |
| 1-a-56 | Me | Me | 3-CHO | — | Me | Z |
| 1-a-57 | Me | Me | 3-CO₂H | — | Me | Z |
| 1-a-58 | Me | Me | 3-NH₂ | — | Me | Z |
| 1-a-59 | Me | Me | 3-(CH=CH₂) | — | Me | Z |
| 1-a-60 | Me | Me | 3-(C≡CH) | — | Me | Z |
| 1-a-61 | Me | Me | 3-Ph | — | Me | Z |
| 1-a-62 | Me | Me | 3-(Py-2-yl) | — | Me | Z |
| 1-a-63 | Me | Me | 3-COMe | — | Me | Z |
| 1-a-64 | Me | Me | 3-CO₂Me | — | Me | Z |
| 1-a-65 | | CH₂CH₂ (form a ring) | — | — | Me | Z |
| 1-a-66 | | CH₂CH₂CH₂ (form a ring) | — | — | Me | Z |
| 1-a-67 | | CH₂C(Me)₂ (form a ring) | — | — | Me | Z |
| 1-a-68 | Et | CN | — | — | Me | Z |
| 1-a-69 | Et | H | — | — | Me | Z |
| 1-a-70 | CH₂C≡CH | CN | — | — | Me | Z |
| 1-a-71 | Me | C(O)Me | — | — | Me | Z |
| 1-a-72 | 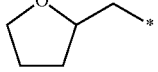 | Me | — | — | Me | Z |
| 1-a-73 | 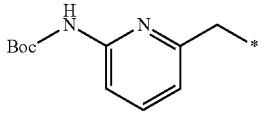 [SMILES: *Cc1cccc(NC(=O)OC(C)(C)C)n1] | Me | — | — | Me | Z |
| 1-a-74 | CH₂C≡CCH₃ | Me | — | — | Me | Z |
| 1-a-75 | CH₂CMe₃ | Me | — | — | Me | Z |
| 1-a-76 | Bn | H | — | — | Me | Z |

TABLE 1-continued
| No. | R^50 | R^51 | $(R)_{n2}$ | $(X)_{n1}$ | Y | E/Z |
|---|---|---|---|---|---|---|
| 1-a-77 | CH$_2$c-Pro | Me | — | — | Me | Z |
| 1-a-78 | i-Pro | Me | — | — | Me | Z |
| 1-a-79 | i-Pro | H | — | — | Me | Z |
| 1-a-80 | Me | C(O)OEt | — | — | Me | Z |
| 1-a-81 | Me | C(O)NMe$_2$ | — | — | Me | Z |
| 1-a-82 | Me | Me | — | 3-F | Me | Z |
| 1-a-83 | Me | Me | — | (3-Me)(4-F) | Me | Z |
| 1-a-84 | Me | Me | 3-Cl | — | Me | Z |
| 1-a-85 | Me | Me | 3,5-Cl | — | Me | Z |
| 1-a-86 | 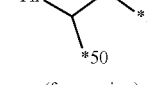 (form a ring) | | — | — | Me | Z |
| 1-a-87 | 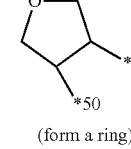 (form a ring) | | — | — | Me | Z |
| 1-a-88 | 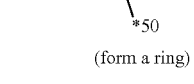 (form a ring) | | — | — | Me | Z |
| 1-a-89 | 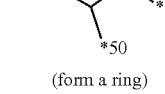 (form a ring) | | — | — | Me | Z |
| 1-a-90 | 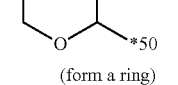 (form a ring) | | — | — | Me | Z |
| 1-a-91 | 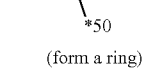 (form a ring) | | — | — | Me | Z |
| 1-a-92 | 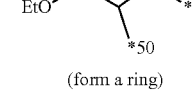 (form a ring) | | — | — | Me | Z |
| 1-a-93 | 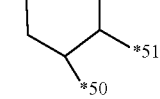 (form a ring) | | — | — | Me | Z |

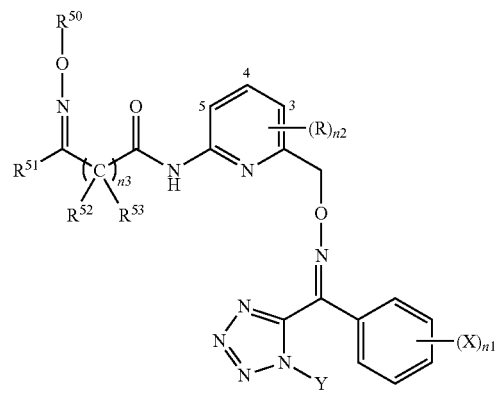

(1-b)

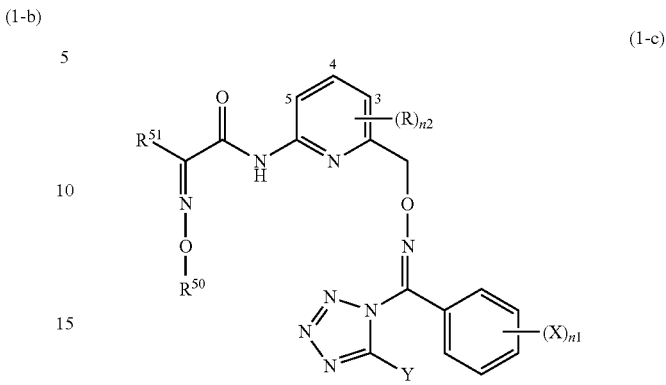

(1-c)

TABLE 2

| | $R^{50}$ | $R^{51}$ | $(C(R^{52})(R^{53}))_{n3}$ | $(R)_{n2}$ | $(X)_{n1}$ | Y | E/Z |
|---|---|---|---|---|---|---|---|
| 1-b-1 | H | H | $CH_2$ | — | — | Me | Z |
| 1-b-2 | H | Me | $CH_2$ | — | — | Me | Z |
| 1-b-3 | Me | Me | $CH_2$ | — | — | Me | Z |
| 1-b-4 | Et | Me | $CH_2$ | — | — | Me | Z |
| 1-b-5 | n-Pro | Me | $CH_2$ | — | — | Me | Z |
| 1-b-6 | $CH_2CH{=}CH_2$ | Me | $CH_2$ | — | — | Me | Z |
| 1-b-7 | $CH_2CH{=}Cl_2$ | Me | $CH_2$ | — | — | Me | Z |
| 1-b-8 | $CH_2C{\equiv}CH$ | Me | $CH_2$ | — | — | Me | Z |
| 1-b-9 | $CH_2CH_2OMe$ | Me | $CH_2$ | — | — | Me | Z |
| 1-b-10 | $CH_2CF_3$ | Me | $CH_2$ | — | — | Me | Z |
| 1-b-11 | $CH_2CH_2CN$ | Me | $CH_2$ | — | — | Me | Z |
| 1-b-12 | Bn | Me | $CH_2$ | — | — | Me | Z |
| 1-b-13 | $CH_2$(Py-2-yl) | Me | $CH_2$ | — | — | Me | Z |
| 1-b-14 | Ph | Me | $CH_2$ | — | — | Me | Z |
| 1-b-15 | Py-2-yl | Me | $CH_2$ | — | — | Me | Z |
| 1-b-16 | Me | Ph | $CH_2$ | — | — | Me | Z |
| 1-b-17 | n-Pro | Ph | $CH_2$ | — | — | Me | Z |
| 1-b-18 | $CH_2CH{=}CH_2$ | Ph | $CH_2$ | — | — | Me | Z |
| 1-b-19 | $CH_2C{\equiv}CH$ | Ph | $CH_2$ | — | — | Me | Z |
| 1-b-20 | $CH_2CH_2OMe$ | Ph | $CH_2$ | — | — | Me | Z |
| 1-b-21 | Me | Py-2-yl | $CH_2$ | — | — | Me | Z |
| 1-b-22 | n-Pro | Py-2-yl | $CH_2$ | — | — | Me | Z |
| 1-b-23 | $CH_2CH{=}CH_2$ | Py-2-yl | $CH_2$ | — | — | Me | Z |
| 1-b-24 | $CH_2C{\equiv}CH$ | Py-2-yl | $CH_2$ | — | — | Me | Z |
| 1-b-25 | $CH_2CH_2OMe$ | Py-2-yl | $CH_2$ | — | — | Me | Z |
| 1-b-26 | Me | $CH_2OMe$ | $CH_2$ | — | — | Me | Z |
| 1-b-27 | n-Pro | $CH_2OMe$ | $CH_2$ | — | — | Me | Z |
| 1-b-28 | $CH_2CH{=}CH_2$ | $CH_2OMe$ | $CH_2$ | — | — | Me | Z |
| 1-b-29 | $CH_2C{\equiv}CH$ | $CH_2OMe$ | $CH_2$ | — | — | Me | Z |
| 1-b-30 | $CH_2CH_2OMe$ | $CH_2OMe$ | $CH_2$ | — | — | Me | Z |
| 1-b-31 | Me | OMe | $CH_2$ | — | — | Me | Z |
| 1-b-32 | Me | CN | $CH_2$ | — | — | Me | Z |
| 1-b-33 | Me | Me | $CH_2$ | — | 2-F | Me | Z |
| 1-b-34 | Me | Me | $CH_2$ | — | 2-$CF_3$ | Me | Z |
| 1-b-35 | Me | Me | $CH_2$ | — | 2,4-$F_2$ | Me | Z |
| 1-b-36 | Me | Me | $CH_2$ | 3-F | — | Me | Z |
| 1-b-37 | Me | Me | $CH_2$ | 3-$CF_3$ | — | Me | Z |
| 1-b-38 | Me | Me | $CF_2$ | — | — | Me | Z |
| 1-b-39 | Me | Me | $CMe_2$ | — | — | Me | Z |
| 1-b-40 | Me | Me | $CH_2CH_2$ | — | — | Me | Z |

TABLE 3

|  | $R^{50}$ | $R^{51}$ | $(R)_{n2}$ | $(X)_{n1}$ | Y | E/Z |
|---|---|---|---|---|---|---|
| 1-c-1 | H | H | — | — | Me | Z |
| 1-c-2 | H | Me | — | — | Me | Z |
| 1-c-3 | Me | Me | — | — | Me | Z |
| 1-c-4 | Et | Me | — | — | Me | Z |
| 1-c-5 | n-Pro | Me | — | — | Me | Z |
| 1-c-6 | $CH_2CH=CH_2$ | Me | — | — | Me | Z |
| 1-c-7 | $CH_2CH=Cl_2$ | Me | — | — | Me | Z |
| 1-c-8 | $CH_2C\equiv CH$ | Me | — | — | Me | Z |
| 1-c-9 | $CH_2CH_2OMe$ | Me | — | — | Me | Z |
| 1-c-10 | $CH_2CF_3$ | Me | — | — | Me | Z |
| 1-c-11 | $CH_2CH_2CN$ | Me | — | — | Me | Z |
| 1-c-12 | Bn | Me | — | — | Me | Z |
| 1-c-13 | $CH_2$(Py-2-yl) | Me | — | — | Me | Z |
| 1-c-14 | Ph | Me | — | — | Me | Z |
| 1-c-15 | Py-2-yl | Me | — | — | Me | Z |
| 1-c-16 | Me | Ph | — | — | Me | Z |
| 1-c-17 | n-Pro | Ph | — | — | Me | Z |
| 1-c-18 | $CH_2CH=CH_2$ | Ph | — | — | Me | Z |
| 1-c-19 | $CH_2C\equiv CH$ | Ph | — | — | Me | Z |
| 1-c-20 | $CH_2CH_2OMe$ | Ph | — | — | Me | Z |
| 1-c-21 | Me | Py-2-yl | — | — | Me | Z |
| 1-c-22 | n-Pro | Py-2-yl | — | — | Me | Z |
| 1-c-23 | $CH_2CH=CH_2$ | Py-2-yl | — | — | Me | Z |
| 1-c-24 | $CH_2C\equiv CH$ | Py-2-yl | — | — | Me | Z |
| 1-c-25 | $CH_2CH_2OMe$ | Py-2-yl | — | — | Me | Z |
| 1-c-26 | Me | $CH_2OMe$ | — | — | Me | Z |
| 1-c-27 | n-Pro | $CH_2OMe$ | — | — | Me | Z |
| 1-c-28 | $CH_2CH=CH_2$ | $CH_2OMe$ | — | — | Me | Z |
| 1-c-29 | $CH_2C\equiv CH$ | $CH_2OMe$ | — | — | Me | Z |
| 1-c-30 | $CH_2CH_2OMe$ | $CH_2OMe$ | — | — | Me | Z |
| 1-c-31 | Me | OMe | — | — | Me | Z |
| 1-c-32 | Me | CN | — | — | Me | Z |
| 1-c-33 | Me | Me | — | 2-F | Me | Z |
| 1-c-34 | Me | Me | — | 2-$CF_3$ | Me | Z |
| 1-c-35 | Me | Me | — | 2,4-$F_2$ | Me | Z |
| 1-c-36 | Me | Me | 3-F | — | Me | Z |
| 1-c-37 | Me | Me | 3-$CF_3$ | — | Me | Z |

[Chemical formula 17]

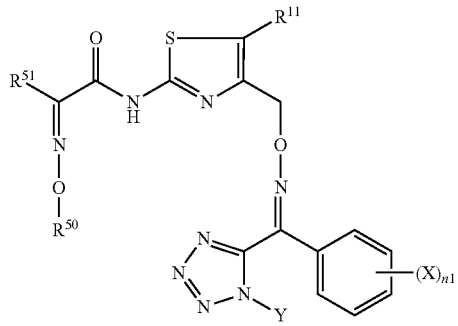

(1-d)

TABLE 4

|  | $R^{50}$ | $R^{51}$ | $R^{11}$ | $(X)_{n1}$ | Y | E/Z |
|---|---|---|---|---|---|---|
| 1-d-1 | H | H | — | — | Me | Z |
| 1-d-2 | H | Me | — | — | Me | Z |
| 1-d-3 | Me | Me | — | — | Me | Z |
| 1-d-4 | Et | Me | — | — | Me | Z |
| 1-d-5 | n-Pro | Me | — | — | Me | Z |
| 1-d-6 | $CH_2CH=CH_2$ | Me | — | — | Me | Z |
| 1-d-7 | $CH_2CH=Cl_2$ | Me | — | — | Me | Z |
| 1-d-8 | $CH_2C\equiv CH$ | Me | — | — | Me | Z |
| 1-d-9 | $CH_2CH_2OMe$ | Me | — | — | Me | Z |
| 1-d-10 | $CH_2CF_3$ | Me | — | — | Me | Z |
| 1-d-11 | $CH_2CH_2CN$ | Me | — | — | Me | Z |

TABLE 4-continued

|  | $R^{50}$ | $R^{51}$ | $R^{11}$ | $(X)_{n1}$ | Y | E/Z |
|---|---|---|---|---|---|---|
| 1-d-12 | Bn | Me | — | — | Me | Z |
| 1-d-13 | $CH_2$(Py-2-yl) | Me | — | — | Me | Z |
| 1-d-14 | Ph | Me | — | — | Me | Z |
| 1-d-15 | Py-2-yl | Me | — | — | Me | Z |
| 1-d-16 | Me | Ph | — | — | Me | Z |
| 1-d-17 | n-Pro | Ph | — | — | Me | Z |
| 1-d-18 | $CH_2CH=CH_2$ | Ph | — | — | Me | Z |
| 1-d-19 | $CH_2C\equiv CH$ | Ph | — | — | Me | Z |
| 1-d-20 | $CH_2CH_2OMe$ | Ph | — | — | Me | Z |
| 1-d-21 | Me | Py-2-yl | — | — | Me | Z |
| 1-d-22 | n-Pro | Py-2-yl | — | — | Me | Z |
| 1-d-23 | $CH_2CH=CH_2$ | Py-2-yl | — | — | Me | Z |
| 1-d-24 | $CH_2C\equiv CH$ | Py-2-yl | — | — | Me | Z |
| 1-d-25 | $CH_2CH_2OMe$ | Py-2-yl | — | — | Me | Z |
| 1-d-26 | Me | $CH_2OMe$ | — | — | Me | Z |
| 1-d-27 | n-Pro | $CH_2OMe$ | — | — | Me | Z |
| 1-d-28 | $CH_2CH=CH_2$ | $CH_2OMe$ | — | — | Me | Z |
| 1-d-29 | $CH_2C\equiv CH$ | $CH_2OMe$ | — | — | Me | Z |
| 1-d-30 | $CH_2CH_2OMe$ | $CH_2OMe$ | — | — | Me | Z |
| 1-d-31 | Me | OMe | — | — | Me | Z |
| 1-d-32 | Me | CN | — | — | Me | Z |
| 1-d-33 | Me | Me | — | 2-F | Me | Z |
| 1-d-34 | Me | Me | — | 2-$CF_3$ | Me | Z |
| 1-d-35 | Me | Me | — | 2,4-$F_2$ | Me | Z |
| 1-d-36 | Me | Me | 3-F | — | Me | Z |
| 1-d-37 | Me | Me | 3-$CF_3$ | — | Me | Z |

[Chemical formula 18]

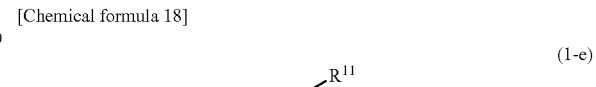

(1-e)

TABLE 5

|  | $R^{50}$ | $R^{51}$ | $R^{11}$ | $(X)_{n1}$ | Y | E/Z |
|---|---|---|---|---|---|---|
| 1-e-1 | H | H | — | — | Me | Z |
| 1-e-2 | H | Me | — | — | Me | Z |
| 1-e-3 | Me | Me | — | — | Me | Z |
| 1-e-4 | Et | Me | — | — | Me | Z |
| 1-e-5 | n-Pro | Me | — | — | Me | Z |
| 1-e-6 | $CH_2CH=CH_2$ | Me | — | — | Me | Z |
| 1-e-7 | $CH_2CH=Cl_2$ | Me | — | — | Me | Z |
| 1-e-8 | $CH_2C\equiv CH$ | Me | — | — | Me | Z |
| 1-e-9 | $CH_2CH_2OMe$ | Me | — | — | Me | Z |
| 1-e-10 | $CH_2CF_3$ | Me | — | — | Me | Z |
| 1-e-11 | $CH_2CH_2CN$ | Me | — | — | Me | Z |
| 1-e-12 | Bn | Me | — | — | Me | Z |
| 1-e-13 | $CH_2$(Py-2-yl) | Me | — | — | Me | Z |
| 1-e-14 | Ph | Me | — | — | Me | Z |
| 1-e-15 | Py-2-yl | Me | — | — | Me | Z |
| 1-e-16 | Me | Ph | — | — | Me | Z |
| 1-e-17 | n-Pro | Ph | — | — | Me | Z |
| 1-e-18 | $CH_2CH=CH_2$ | Ph | — | — | Me | Z |
| 1-e-19 | $CH_2C\equiv CH$ | Ph | — | — | Me | Z |
| 1-e-20 | $CH_2CH_2OMe$ | Ph | — | — | Me | Z |
| 1-e-21 | Me | Py-2-yl | — | — | Me | Z |
| 1-e-22 | n-Pro | Py-2-yl | — | — | Me | Z |

TABLE 5-continued

| | $R^{50}$ | $R^{51}$ | $R^{11}$ | $(X)_{n1}$ | Y | E/Z |
|---|---|---|---|---|---|---|
| 1-e-23 | $CH_2CH=CH_2$ | Py-2-yl | — | — | Me | Z |
| 1-e-24 | $CH_2C≡CH$ | Py-2-yl | — | — | Me | Z |
| 1-e-25 | $CH_2CH_2OMe$ | Py-2-yl | — | — | Me | Z |
| 1-e-26 | Me | $CH_2OMe$ | — | — | Me | Z |
| 1-e-27 | n-Pro | $CH_2OMe$ | — | — | Me | Z |
| 1-e-28 | $CH_2CH=CH_2$ | $CH_2OMe$ | — | — | Me | Z |
| 1-e-29 | $CH_2C≡CH$ | $CH_2OMe$ | — | — | Me | Z |
| 1-e-30 | $CH_2CH_2OMe$ | $CH_2OMe$ | — | — | Me | Z |
| 1-e-31 | Me | OMe | — | — | Me | Z |
| 1-e-32 | Me | CN | — | — | Me | Z |
| 1-e-33 | Me | Me | — | 2-F | Me | Z |
| 1-e-34 | Me | Me | — | $2-CF_3$ | Me | Z |
| 1-e-35 | Me | Me | — | $2,4-F_2$ | Me | Z |
| 1-e-36 | Me | Me | 3-F | — | Me | Z |
| 1-e-37 | Me | Me | $3-CF_3$ | — | Me | Z |

[Chemical formula 19]

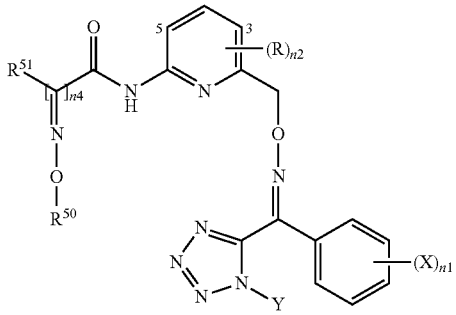

(1-f)

TABLE 6

| No. | $R^{50}$ | n4 | $R^{51}$ | $(R)_{n2}$ | $(X)_{n1}$ | Y | E/Z |
|---|---|---|---|---|---|---|---|
| 1-f-1 | Me | 2 | Me | — | — | Me | Z |

[Chemical formula 20]

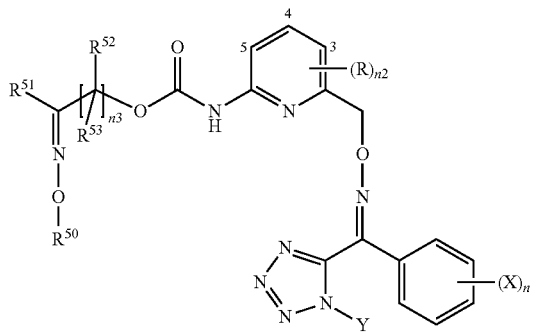

(1-g)

TABLE 7

| No. | $R^{50}$ | $R^{51}$ | $(C(R^{52})(R^{53}))_{n3}$ | $(R)_{n2}$ | $(X)_{n1}$ | Y | E/Z |
|---|---|---|---|---|---|---|---|
| 1-g-1 | Et | Me | $CH_2$ | — | — | Me | Z |
| 1-g-2 | Et | Me | $(CH_2)_2$ | — | — | Me | Z |
| 1-g-3 | Et | Me | $(CH_2)_3$ | — | — | Me | Z |
| 1-g-4 | n-Pro | Me | $CH(CH_3)$ | — | — | Me | Z |
| 1-g-5 | n-Pro | Me | $C(CH_3)_2$ | — | — | Me | Z |
| 1-g-6 | Et | H | $CH_2$ | — | — | Me | Z |
| 1-g-7 | (form a ring *50–*51, neopentyl-like) | | $C(CH_3)_2$ | — | — | Me | Z |
| 1-g-8 | (form a ring *50–*51, neopentyl-like) | | $CH(CH_3)$ | — | — | Me | Z |

Some of the measured results such as $^1$H-NMR, melting point or the like of the compounds obtained in the Examples are shown below.

(Compound 1-a-16)
 AMR;
 $^1$H-NMR: 4.02 (s, 3H), 4.10 (s, 3H), 5.32 (s, 2H), 7.05 (d, 1H), 7.35-7.51 (m, 10H), 7.67 (t, 1H), 8.19 (d, 1H), 9.28 (br-s, 1H).

(Compound 1-b-3)
 AMR;
 $^1$H-NMR: A:B=3:2 isomer mixture 1.97 (A) & 2.02 (B) (s, 3H), 3.31 (A) & 3.48 (B) (s, 2H), 3.92-3.99 (A&B) (m, 6H), 5.27 (A&B) (s, 2H), 7.01 (A&B) (m, 1H), 7.34-7.52 (A&B) (m, 5H), 7.69 (A&B) (m, 1H), 8.09 (A&B) (m, 1H), 8.43 (A) & 8.55 (B) (br-s, 1H).

(Compound 1-a-21)
 VISC. OIL;
 $^1$H-NMR: 3.97 (s, 3H), 4.10 (s, 3H), 5.28 (s, 2H), 7.07 (d, 1H), 7.29-7.52 (m, 6H), 7.11-7.78 (m, 2H), 7.87 (d, 1H), 8.31 (d, 1H), 8.56 (br-s, 1H), 8.60-8.63 (m, 1H).

(Compound 1-a-26)
 VISC. OIL;
 $^1$H-NMR: 3.42 (s, 3H), 3.99 (s, 3H), 4.13 (s, 3H), 4.41 (s, 2H), 5.30 (s, 2H), 7.04 (d, 1H), 7.30-7.52 (m, 5H), 7.73 (t, 1H), 8.20 (d, 1H), 9.04 (br-s, 1H).

(Compound 1-a-8)
 Melting point: 107-109° C.;

(Compound 1-a-6)
 nD20.2: 1.5753

(Compound 1-a-9)
 nD20.3: 1.5634

(Compound 1-a-65)
 VISC. OIL;
 $^1$H-NMR: 3.30 (t, 2H), 4.01 (s, 3H), 4.60 (t, 2H), 5.29 (s, 2H), 7.04 (d, 1H), 7.34-7.53 (m, 5H), 7.73 (t, 1H), 8.12 (d, 1H), 8.97 (br-s, 1H).

(Compound 1-a-67)
 VISC. OIL;
 $^1$H-NMR: 1.50 (s, 6H), 3.05 (s, 2H), 4.01 (s, 3H), 5.29 (s, 2H), 7.03 (d, 1H), 7.34-7.54 (m, 5H), 7.72 (t, 1H), 8.12 (d, 1H), 8.96 (br-s, 1H).

(Compound 1-a-68)
 VISC. OIL;
 1.48 (t, 3H), 3.99 (s, 3H), 4.61 (q, 2H), 5.30 (s, 2H), 7.10 (d, 1H), 7.35-7.51 (m, 5H), 7.77 (t, 1H), 8.15 (d, 1H), 8.80 (br-s, 1H).

(Compound 1-a-69)
VISC. OIL;
1.36 (t, 3H), 4.00 (s, 3H), 4.32 (q, 2H), 5.30 (s, 2H), 7.04 (d, 1H), 7.34-7.52 (m, 6H), 7.73 (t, 1H), 8.17 (d, 1H), 8.84 (br-s, 1H).
(Compound 1-a-70)
VISC. OIL;
2.71 (t, 1H), 4.00 (s, 3H), 5.09 (d, 2H), 5.31 (s, 2H), 7.11 (d, 1H), 7.24-7.51 (m, 5H), 7.78 (t, 1H), 8.14 (d, 1H), 8.81 (br-s, 1H).
(Compound 1-a-71)
VISC. OIL;
2.46 (s, 3H), 3.98 (s, 3H), 4.16 (s, 3H), 5.27 (s, 2H), 7.06 (d, 1H), 7.35-7.51 (m, 5H), 7.73 (t, 1H), 8.18 (d, 1H), 8.22 (br-s, 1H).
(Compound 1-a-72)
VISC. OIL;
1.67-2.09 (m, 4H), 2.13 (s, 3H), 3.79-3.96 (m, 2H), 4.00 (s, 3H), 4.23-4.31 (m, 1H), 5.30 (s, 2H), 7.02 (d, 1H), 7.35-7.53 (m, 5H), 7.72 (t, 1H), 8.18 (d, 1H), 9.10 (s, 1H).
(Compound 1-a-73)
VISC. OIL;
1.52 (s, 9H), 2.18 (s, 3H), 3.99 (s, 3H), 5.27 (s, 2H), 5.28 (s, 2H), 6.99-7.74 (m, 9H), 7.87 (d, 1H), 8.16 (d, 1H), 9.05 (br-s, 1H).
(Compound 1-a-74)
VISC. OIL;
1.89 (s, 3H), 2.12 (s, 3H), 4.02 (s, 1H), 4.79-4.84 (m, 2H), 5.30 (s, 2H), 7.03 (d, 1H), 7.34-7.52 m, 5H), 7.72 (t, 1H), 8.18 (d, 1H), 9.11 (s, 1H).
(Compound 1-a-75)
VISC. OIL;
1.00 (s, 9H), 2.09 (s, 3H), 3.99-4.01 (m, 5H), 5.31 (s, 2H), 7.03 (d, 1H), 7.30-7.52 (m, 5H), 7.72 (t, 1H), 8.19 (d, 1H), 9.23 (s, 1H).
(Compound 1-a-76)
VISC. OIL;
3.96 (s, 3H), 5.31 (s, 2H), 7.01-8.18 (m, 14H), 9.09 (s, 1H).
(Compound 1-a-77)
AMR;
0.32-0.37 (m, 2H), 0.59-0.65 (m, 2H), 1.20-1.26 (m, 1H), 2.19 (s, 3H), 3.99 (s, 3H), 4.09 (d, 2H), 5.30 (s, 2H), 7.02 (d, 1H), 7.34-7.75 (m, 5H), 8.18 (d, 1H), 9.13 (s, 1H).
(Compound 1-a-78)
AMR;
1.28-1.35 (m, 6H), 2.08 (s, 3H), 4.00 (s, 3H), 4.50-4.58 (m, 1H), 5.30 (s, 2H), 7.02 (d, 1H), 7.34-7.74 (m, 5H), 8.19 (d, 1H), 9.13 (s, 1H).
(Compound 1-a-79)
VISC. OIL;
1.28-1.35 (m, 6H), 4.11 (s, 3H), 4.50-4.58 (m, 1H), 5.30 (s, 2H), 7.03 (d, 1H), 7.35-7.79 (m, 5H), 7.73 (t, 1H), 8.18 (d, 1H), 8.85 (s, 1H).
(Compound 1-a-80)
AMR;
1.38 (t, 3H), 3.99 (s, 3H), 4.42 (q, 2H), 5.30 (s, 2H), 7.07 (d, 1H), 7.35-7.52 (m, 5H), 7.73 (t, 1H), 8.14 (d, 1H), 8.83 (br-s, 1H).
(Compound 1-a-81)
VISC. OIL;
2.94 (s, 3H), 3.08 (s, 3H), 4.00 (s, 3H), 4.12 (s, 3H), 5.30 (s, 2H), 7.06 (d, 1H), 7.35-7.52 (m, 5H), 7.73 (t, 1H), 8.15 (d, 1H), 8.93 (br-s, 1H).
(Compound 1-a-82)
nD20.4: 1.5601
(Compound 1-a-83)
AMR;
2.09 (s, 3H), 2.46 (s, 3H), 4.00 (s, 3H), 4.08 (s, 3H), 5.30 (s, 2H), 5.25 (s, 2H), 6.91 (d, 1H), 6.98 (t, 1H), 7.28-7.36 (m, 3H), 7.48 (br-s, 1H), 7.63 (t, 1H), 7.88 (d, 1H).
(Compound 1-a-84)
Melting point: 159-161° C.;
(Compound 1-a-85)
Melting point: 113-115° C.;
(Compound 1-a-86)
VISC. OIL;
3.21-42 (m, 2H), 4.01 (s, 3H), 4.82-4.90 (m, 1H), 5.29 (s, 2H), 7.04-7.75 (m, 12H), 8.13 (d, 1H), 8.93 (br-s, 1H).
(Compound 1-a-87)
Melting point: 78-79° C.;
(Compound 1-a-88)
VISC. OIL;
3.06-3.59 (m, 7H), 4.01 (s, 3H), 4.95-5.02 (m, 1H), 5.34 (s, 2H), 7.09 (d, 1H), 7.35-7.77 (m, 5H), 7.80 (t, 1H), 8.18 (d, 1H), 9.01 (br-s, 1H).
(Compound 1-a-89)
VISC. OIL;
1.20 (t, 3H), 1.76 (tq, 2H), 1.89 (dt, 2H), 3.21-3.42 (m, 2H), 4.01 (s, 3H), 4.95-5.02 (m, 1H), 5.34 (s, 2H), 7.09 (d, 1H), 7.35-7.77 (m, 5H), 7.80 (t, 1H), 8.18 (d, 1H), 9.01 (br-s, 1H).
(Compound 1-a-90)
VISC. OIL;
1.26-71 (m, 7H), 3.50-3.61 (m, 2H), 4.00 (s, 3H), 4.40-4.45 (m, 1H), 5.28 (s, 2H), 7.09-7.51 (m, 7H), 7.76 (t, 1H), 8.18 (d, 1H), 9.36 (br-s, 1H).
(Compound 1-a-91)
Melting point: 70-71° C.;
(Compound 1-a-92)
VISC. OIL;
1.20 (t, 3H), 1.28 (t, 3H), 3.21-3.79 (m, 6H), 4.01 (s, 3H), 4.54 (d, 1H), 4.82-4.90 (m, 1H), 5.29 (s, 2H), 7.04 (d, 1H), 7.35-7.53 (m, 5H), 7.72 (t, 1H), 8.13 (d, 1H), 8.93 (s, 1H).
(Compound 1-a-93)
VISC. OIL;
0.83-2.17 (m, 8H), 2.98-3.62 (m, 2H), 4.01 (s, 1H), 5.29 (s, 2H), 7.03 (d, 1H), 7.35-7.52 (m, 5H), 7.72 (t, 1H), 8.13 (d, 1H), 8.97 (s, 1H).
(Compound 1-f-1)
AMR;
2.04 (s, 3H), 3.92 (s, 3H), 3.97 (s, 3H), 3.99 (s, 3H), 5.27 (s, 2H), 7.05 (d, 1H), 7.35-7.52 (m, 5H), 7.74 (t, 1H), 8.00 (br-s, 1H), 8.21 (d, 1H).
(Compound 1-g-1)
AMR;
1.24 (t, 3H), 1.89 (s, 3H), 3.97 (s, 3H), 4.11 (q, 2H), 4.70 (s, 2H), 5.28 (s, 2H), 6.98 (d, 2H), 7.33-7.51 (m, 5H), 7.69 (dd, 1H), 7.90 (d, 1H).
(Compound 1-g-2)
nD20.3: 1.5245
(Compound 1-g-3)
nD20.2: 1.5216
(Compound 1-g-4)
VISC. OIL;
0.92 (t, 3H), 1.44 (d, 3H), 1.66 (tq, 2H), 1.86 (s, 3H), 3.96 (s, 3H), 4.02 (t, 3H), 5.26 (s, 2H), 5.41 (q, 1H), 6.96 (d, 1H), 7.38-7.53 (m, 6H), 7.68 (dd, 1H), 7.99 (d, 1H).
(Compound 1-g-5)
Melting point: 111-112° C.;
(Compound 1-g-6)
AMR;
1.24-1.29 (m, 3H), 3.97 (s, 3H), 4.09-4.20 (m, 2H), 4.76 (d, 1H, J=5.95 Hz, Z or E isomer), 4.97 (d, 1H, J=3.87 Hz, Z or E isomer), 5.26-5.27 (m, 2H), 6.81 (t, 0.5H, J=3.87 Hz, Z or E isomer), 6.98 (d, 1H, J=7.14 Hz), 7.34-7.51 (m, 6.5H), 7.66-7.72 (m, 1H), 7.87-7.90 (d, 1H, J=8.33 Hz).
(Compound 1-g-7)
 Melting point: 65-68° C.;
(Compound 1-g-8)
 Melting point: 65-68° C.

The following indicates several preparation examples of the plant disease control agent of the present invention. However, additives and addition rates are not limited to those used in these examples, and can be changed over a wide range. The term "parts" used in the preparation examples refers to parts by mass.

Preparation Example 1

Wettable Powder

| | |
|---|---|
| Compound of present invention | 40 parts |
| Clay | 53 parts |
| Sodium dioctylsulfosuccinate | 4 parts |
| Sodium lignin sulfonate | 3 parts |

The above components were mixed and finely crushed to obtain a wettable powder containing 40% of the active ingredient.

Preparation Example 2

Emulsion

| | |
|---|---|
| Compound of present invention | 10 parts |
| Solvesso 200 | 53 parts |
| Cyclohexanone | 26 parts |
| Calcium dodecylbenzenesulfonate | 1 part |
| Polyoxyethylene alkyl allyl ether | 10 parts |

The above components were mixed and dissolved to obtain an emulsion containing 10% of the active ingredient.

Preparation Example 3

Powder

| | |
|---|---|
| Compound of present invention | 10 parts |
| Clay | 90 parts |

The above components were uniformly mixed and finely crushed to obtain a powder containing 10% of the active ingredient.

Preparation Example 4

Granules

| | |
|---|---|
| Compound of present invention | 5 parts |
| Clay | 73 parts |
| Bentonite | 20 parts |
| Sodium dioctylsulfosuccinate | 1 part |
| Potassium phosphate | 1 part |

The above components were crushed and mixed followed by the addition of water, mixing well, granulating and drying to obtain granules containing 5% of the active ingredient.

Preparation Example 5

Suspension

| | |
|---|---|
| Compound of present invention | 10 parts |
| Polyoxyethylene alkyl allyl ether | 4 parts |
| Sodium polycarbonate | 2 parts |
| Glycerin | 10 parts |
| Xanthan gum | 0.2 parts |
| Water | 73.8 parts |

The above components were mixed and wet-crushed to a particle size of 3 microns or less to obtain a suspension containing 10% of the active ingredient.

Preparation Example 6

Granulated Wettable Powder

| | |
|---|---|
| Compound of present invention | 40 parts |
| Clay | 36 parts |
| Potassium chloride | 10 parts |
| Sodium alkylbenzenesulfonate | 1 part |
| Sodium lignin sulfonate | 8 parts |
| Formaldehyde condensate of sodium alkylbenzenesulfonate | 5 parts |

The above components were uniformly mixed and finely crushed followed by adding a suitable amount of water and mixing to form a clay-like substance. The clay-like substance was then granulated and then dried to obtain a granulated wettable powder containing 40% of the active ingredient.

Test Example 1

Tomato Late Blight (PN) Preventive Effect Test

Tomato seedlings (variety: Regina, 4th to 5th leaf term) cultivated in terracotta pots were sprayed with the emulsion of Preparation Example 2 described above at an active ingredient concentration of 100 ppm. After spraying, the plants were allowed to air dry at room temperature, and the test plants were inoculated by spraying with a suspension of zoosporangia of tomato late blight pathogen (*Phytophthora infestans*) and holding for 4 days in a high-humidity, constant temperature chamber (20° C.) at a light/dark cycle of 12 hours. The appearance of lesion on the leaves was compared with untreated plants to determine control effects (protective value).

The PN preventive effect tests were performed on the following compounds, and all compounds showed a protective value of 90% or more.

Compound: 1-a-3, 1-a-5, 1-a-6, 1-a-8, 1-a-9, 1-a-12, 1-a-16, 1-a-21, 1-a-26, 1-a-65, 1-a-67, 1-b-3, 1-a-68, 1-a-69, 1-a-70, 1-a-71, 1-a-72, 1-a-74, 1-a-76, 1-a-77, 1-a-78, 1-a-79, 1-a-80, 1-a-81, 1-a-82, 1-a-83, 1-a-86, 1-a-87, 1-a-88, 1-a-89, 1-a-91, 1-a-92, 1-a-93, 1-f-1, 1-g-1, 1-g-2, 1-g-3, 1-g-4, 1-g-5, 1-g-6, 1-g-7, 1-g-8

Protective value (%)=(degree of infection in untreated area−degree of infection in treated area)/(degree of infection in untreated area)×100

Test Example 2

Antibacterial Test

The compound was dissolved in dimethyl sulfoxide and diluted to double concentration of a predetermined concentration using PSY medium to prepare a chemical liquid. The chemical liquid was placed in 96-well microplates. Meanwhile, as an untreated area, a solution of dimethyl sulfoxide diluted using PSY medium was prepared.

A liquid cultured test fungus (*Pythium aphanidermatum*) suspension was mixed with the chemical liquid in equal amount, and cultured in the dark at 25° C. The amounts of mycelia growth after 3-7 days of cultivation were observed to obtain mycelia elongation inhibition rate.

The antibacterial tests were performed on the following compounds: 1-a-5, 1-a-6, 1-a-8, 1-a-9, 1-a-12, 1-a-16, 1-a-26, 1-a-65, 1-a-67, 1-a-68, 1-a-69, 1-a-70, 1-a-73, 1-a-74, 1-a-75, 1-a-76, 1-a-77, 1-a-78, 1-a-79, 1-a-80, 1-a-82, 1-a-83, 1-a-84, 1-a-85, 1-a-86, 1-a-88, 1-a-89, 1-a-92, 1-f-1, 1-g-1, 1-g-2, 1-g-3, 1-g-4, 1-g-5, 1-g-7, 1-g-8, and all compounds demonstrated a mycelia elongation inhibition rate of 50% or more at the compound concentration of 1 ppm.

As described above, it is apparent that the tetrazolyl oxime derivative or salt thereof of the present invention, as long as Z represents a group represented by formula (a), even if the groups other than Z were modified, still demonstrates a control effect against plant disease, although the effects are stronger or weaker to some degree.

INDUSTRIAL APPLICABILITY

Since the plant disease control agent of the present invention contains the tetrazolyl oxime derivative or salt thereof of the present invention, it allows the plant disease control agent to be effective in controlling disease in cultivation of agricultural and horticultural crops, prevent chemical damage to crops and environmental contamination, and to reduce toxicity to humans, livestock or marine life, thereby making it industrially useful.

The invention claimed is:

1. A tetrazolyl oxime derivative represented by formula (1-a) or (1-c), or salt thereof:

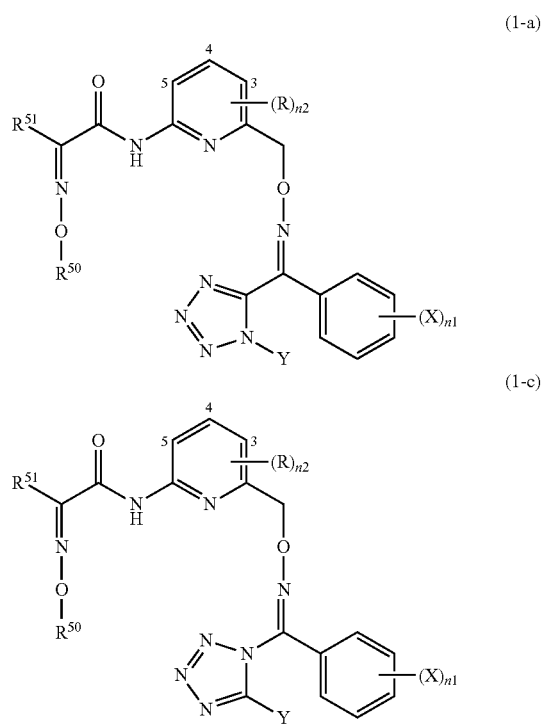

wherein X represents a halogen atom;
n1 represents an integer of 0 to 5, when n1 is 2 or more, plural X may be the same or different from each other;
wherein Y represents a C1-8 alkyl group,
wherein R represents a halogen atom, optionally substituted amino group, C1-8 alkyl group, C1-4 alkoxy group, or C1-4 alkyl thio group;
n2 represents an integer of 0 to 3, when n2 is 2 or more, plural R may be the same or different;
wherein $R^{50}$ represents a hydrogen atom, optionally substituted C1-8 alkyl group, optionally substituted C2-8 alkenyl group, optionally substituted C2-8 alkynyl group;
$R^{51}$ represents a hydrogen atom, optionally substituted C1-8 alkyl group, cyano group;
the substituted amino group is a methyl amino group, dimethyl amino group, methyl ethyl amino group, diethyl amino group, t-butoxycarbonyl methyl amino group, t-butoxycarbonyl amino group, acetyl methyl amino group, acetyl ethyl amino group, or benzoyl methyl amino group,
the substituted C1-8 alkyl group is a chloromethyl group, methoxymethyl group, methyl thiomethyl group, methyl sulfonyl methyl group, dimethyl aminomethyl group, trichloromethyl group, trifluoromethyl group, or 2-chloroethyl group,
the substituted C2-8 alkenyl group is a 2-chloroethenyl group, 2-fluoroethenyl group, 3,3,3-trifluoro-1-pentenyl group, 1,2,2-trifluoroethenyl group, 2,3,3-trifluoro-2-propenyl group, 2,3,3-triiodo-2-propenyl group, or 2-methoxyethenyl group,
the substituted C2-8 alkynyl group is a 2-chloroethynyl group, 2-fluoroethynyl group, 3-fluoro-1-propynyl group, 3,3,3-trifluoro-1-propynyl group, 3-fluoro-2-propynyl group, or 3-iodo-2-propynyl group.

2. The tetrazolyl oxime derivative or salt thereof according to claim 1, wherein n1 represents 0.

3. The tetrazolyl oxime derivative or salt thereof according to claim 1, wherein Y represents a methyl group.

4. A plant disease control composition comprising as an active ingredient thereof the tetrazolyl oxime derivative or salt thereof according to any one of claims 1 to 3 and a surfactant.

\* \* \* \* \*